United States Patent [19]

Nakayama et al.

[11] Patent Number: 4,921,783

[45] Date of Patent: May 1, 1990

[54] SILVER HALIDE PHOTOGRAPHIC LIGHT-SENSITIVE MATERIAL

[75] Inventors: Noritaka Nakayama; Toyoaki Masukawa, both of Hino, Japan

[73] Assignee: Konica Corporation, Tokyo, Japan

[21] Appl. No.: 371,831

[22] Filed: Jun. 20, 1989

Related U.S. Application Data

[63] Continuation-in-part of Ser. No. 280,001, Dec. 5, 1988, abandoned.

[30] Foreign Application Priority Data

Dec. 10, 1987 [JP] Japan .................................. 62-312672
Apr. 18, 1988 [JP] Japan .................................. 63-96332

[51] Int. Cl.$^5$ ............................................. G03C 7/38
[52] U.S. Cl. ................................... 430/558; 430/384; 430/385
[58] Field of Search ...................... 430/384, 385, 558 R

[56] References Cited

U.S. PATENT DOCUMENTS 2,296,271  9/1942  Dawson ............................ 430/558
4,818,672  4/1989  Masukawa ....................... 430/558 R

FOREIGN PATENT DOCUMENTS 1545507  5/1979  United Kingdom .

Primary Examiner—Richard L. Schilling
Attorney, Agent, or Firm—Jordan B. Bierman

[57]    ABSTRACT

A silver halide photographic light-sensitive material is disclosed which comprises a silver halide emulsion layer containing a novel cyan dye-forming coupler. The photographic material is improved in color reproducibility of color images formed thereon. The coupler is represented by the following Formula I.

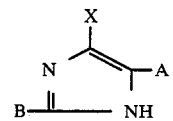

Formula I wherein A is an organic group combined with the imidazole ring by a carbon atom, a nitrogen atom, an oxygen atom or a sulfur atom contained in these group; B is an

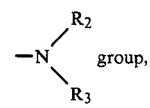

group, a —L—R$_4$ group or a

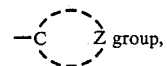

group, in which $R_2$ and $R_3$ are each a hydrogen atom or a substituent, provided that $R_2$ and $R_3$ are allowed to bind to complete a ring; L is an oxygen atom or a sulfur atom; $R_4$ is a hydrogen atom or a substituent; and Z is a group of non-metal atoms necessary to form a five to seven-member heterocyclic ring which contains an oxygen atom, a sulfur atom or a nitrogen atom; X is a hydrogen atom, or a group capable of being split off upon reaction with the oxidation product of a color developing agent.

24 Claims, 1 Drawing Sheet

SILVER HALIDE PHOTOGRAPHIC LIGHT-SENSITIVE MATERIAL

This application is a continuation-in-part of application Ser. No. 280,001, filed Dec. 5, 1988, now abandoned.

FIELD OF THE INVENTION

The present invention relates to a silver halide photographic light-sensitive material that contains a novel cyan coupler.

BACKGROUND OF THE INVENTION

Usually, a silver halide color photographic light-sensitive material contains a light-sensitive silver halide emulsion, as well as a so-called dye forming coupler that is capable of forming a dye upon reaction with an oxidation product of a color developing agent.

As cyan couplers, phenols and naphthols have been in wide use, some of these products being described, for example, in U.S. Pat. Nos. 2,369,929 and 2,474,293.

The cyan dye images formed from such phenols or naphthols, however, pose a serious problem in color reproduction. An absorption spectrum of a cyan dye formed thereby shows a disorderly boundary on the shorter wavelength side and has an undesirable irregular absorption in the green region and partly in the blue region. As a solution to this problem, it has been a usual practice, in negative films, to compensate the irregular absorption by masking using colored couplers. This practice, however, incurs retrogression in sensitivity. With respect to sensitive materials in the reversal system, as well as with color paper, color reproducibility remains impaired due to a lack in effective means for compensation.

SUMMARY OF THE INVENTION

It is an object of the present invention to provide a silver halide photographic light-sensitive material that contains a novel cyan coupler designed to form a cyan dye having a satisfactory spectrum absorption characteristic featuring a sharp boundary on the shorter wavelength side and minimization of the irregular absorption in the green and blue regions.

Another object of the present invention is to provide a silver halide photographic light-sensitive material that contains a cyan coupler capable of forming a cyan dye of high color density, i.e. an excellent color forming capability.

The above-mentioned objects can be accomplished by a silver halide photographic light sensitive material comprising a support provided thereon with a silver halide emulsion layer, wherein said silver halide emulsion layer contains a cyan coupler represented by the following formula I.

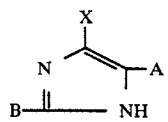

Formula I wherein A is an organic group combined with the imidazole ring by a carbon atom, a nitrogen atom, an oxygen atom or a sulfur atom contained in these group; B is an

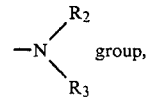

a —L—R$_4$ group or a

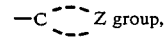

in which R$_2$ and R$_3$ are each a hydrogen atom or a substituent, provided that R$_2$ and R$_3$ are allowed to bind to complete a ring; L is an oxygen atom or a sulfur atom; R$_4$ is a hydrogen atom or a substituent; and Z is a group of non-metal atoms necessary to form a five to seven-member heterocyclic ring which contains an oxygen atom, a sulfur atom or a nitrogen atom; X is a hydrogen atom, or a group capable of being split off upon reaction with the oxidation product of a color developing agent.

DETAILED DESCRIPTION OF THE INVENTION

Figure 1:
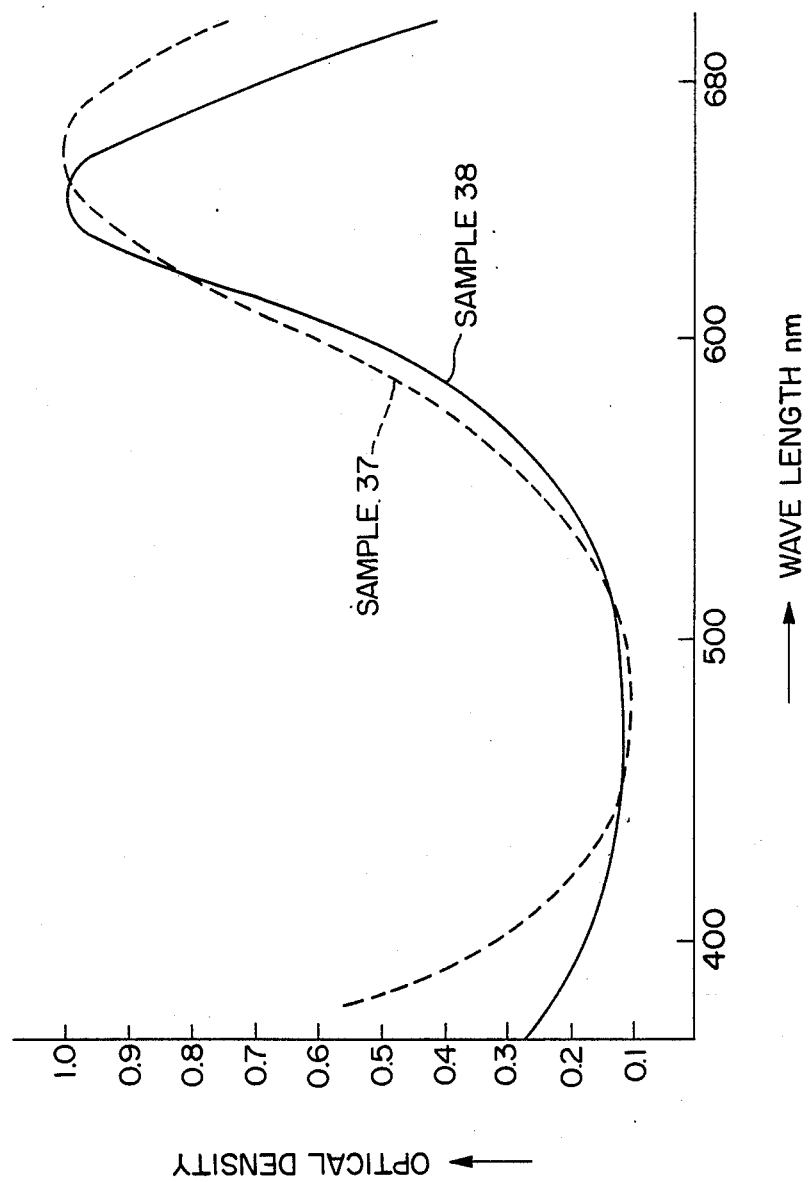
FIG. 1 shows transmittancy spectrum curves for describing the difference between the cyan coupler 60 (Sample 38) of the present invention and a cyan coupler CC-2 (Sample 37) of a comparative example.

The following describes a coupler represented by formula I.

In formula I, A represents an organic group combined with the imidazole ring via a carbon atom, a nitrogen atom, an oxygen atom, or a sulfur atom. The groups represented by A preferably include an alkyl group, an aryl group and a heterocyclic group, and in particular a phenyl group, which include one having a substituent.

B is an

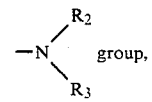

a —L—R$_4$ group or a

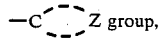

in which R$_2$ and R$_3$ are each a hydrogen atom or a substituent, provided that R$_2$ and R$_3$ are allowed to bind to complete a ring, L is an oxygen atom or a sulfur atom and R$_4$ is a hydrogen atom or a substituent, and Z is a group of non-metal atoms necessary to form a five to seven-member heterocyclic ring which contains an oxygen atom, a sulfur atom or a nitrogen atom. In these substituent, R$_2$ and R$_3$ preferably are each a hydrogen atom, alkyl group or aryl group. R$_2$ and R$_3$ may also be bound together to form a heterocyclic ring.

Preferable as an alkyl group for either of R$_2$ and R$_3$ is one having the straight or branched chain with 1 to 32 carbon atoms, including a cycloalkyl group such as cyclohexyl group. These alkyl groups are allowed to have a substituent, preferable substituent being a halogen atom; groups of hydroxyl, corboxy, cyano, and sulfo; and alkoxy groups with 1 to 22 carbon atoms.

Preferable as an aryl group for either of $R_2$ and $R_3$ is phenyl group or a substituted phenyl group having a group of nitro, amido, sulfonamide, or the like as a substituent group.

Preferable as a heterocycle formed as a result of the bonding between $R_2$ and $R_3$ is a five- or six-membered ring.

In formula I, $R_4$ preferably represents a hydrogen atom, an alkyl group, an aryl group or a heterocyclic group.

Example of the alkyl and aryl groups respectively include the same alkyl or aryl groups as $R_2$ or $R_3$.

Examples of the preferred heterocyclic group are five- or six-membered rings such as groups of 2-pyridyl, 4-pyridyl, 2-benzoimidazolyl, 3,5-dimethyl-1-pyrazolyl, 4-morpholino, 3,5-dimethyl-2-furyl, 2,4-dimethyl-5-thiazolyl, 2-acetamido-4-methyl-5-pyrimidinyl, etc.

The substituent represemnted by

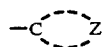

in formula I is a five- to seven member heterocyclic group containing an oxygen atom, sulfur atom or a nitrogen atom. The heterocyclic group preferably includes groups of franyl. thiophenyl, pyrrolyl, axazolyl, iso-oxazolyl, thiazolyl, imidazolyl, triazolyl, tetrazolyl, pyridinyl, pyrimidinyl and 1,3,5-triazinyl and the like. The group represented by

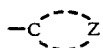

may have a substituent.

In formula I, X represents a hydrogen atom, or a group capable of being split off upon reaction with an oxidation product of a color developing agent.

Examples of those applicable as a group represented by X, which is capable of being split off upon reaction with an oxidation product of a color developing agent, include harogen atoms such as of chlorine, bromine, and fluorine; and groups of hydroxyl, alkoxy, aryloxy, hetrocyclic oxy, acyloxy, sulfonyloxy, alkoxycarbonyloxy, aryloxycarbonyl, alkyloxyarylyoxy, alkoxyoxyaryloxy, alkylthio, mercapto, arylthio, heterocyclic thio, alkoxythiocarbonylthio, acylamino, substituted amino, heterocycle with a nitrogen atom as a bond, sulfonamido, alkyloxycarbonylamino, aryloxycarbonylamino, and carboxyl. Among these examples, a preferred one is a halogen atom, and the most preferable a chlorine atom.

Among the compounds represented by formula I, usefull examples are those expressed by the following formulas II, III and VI in which A is an aryl group, particular, a phenyl group.

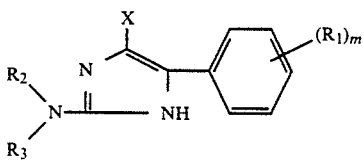

Formula II

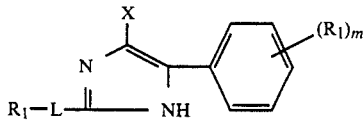

Formula III

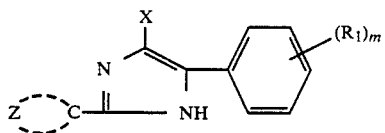

Formula VI

In formulas II, III and VI, $R_1$ is a substituent group, m represents numerals 0 to 5, and $R_2$, $R_3$, $R_4$, L, Z and X are the same as in formula I.

The following describes in detail the compound represented by formula II. There is no specific restriction to the substitutent groups represented by $R_1$ in formula II. Some useful examples include halogen atoms, and groups of cyano, nitro, carboxyl, alkyl, alkoxy, carbamoyl, sulfamoyl, acyl, acyloxy, alkoxycarbonyl,

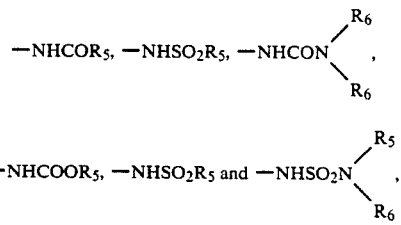

In the above formulas, $R_5$ and $R_6$ individually represent an alkyl group or an aryl group with 1 to 22 carbon atoms. The alkyl group and aryl group represented by the $R_5$ and $R_6$ include an alkyl group and aryl group having a substituent, respectively.

Preferable as an alkyl group represented by $R_1$ is one of the straight chain or branched types with 1 to 22 carbon atoms, examples being methyl, ethyl, butyl, and dodecyl groups. The alkyl groups include cycloalkyls, such as cyclohexyl, and also substituted alkyls, preferable substituent groups in the latter case being, for example, a halogen atom, hydroxyl, carboxyl, cyano, and also sulfo; or alkoxy with 1 to 22 carbon atoms.

Preferable as an alkoxy group is one of the straight chain or branched type with 1 to 22 carbon atoms, examples being the groups of methoxy, ethoxy, i-propyloxy, octyloxy and dodecyloxy.

Examples of the carbamoyl groups are the unsubstituted alkylcarbamoyl groups, such as ethylcarbamoyl and dodecylcarbamoyl, and the substituted alkylcarbamoyl groups, such as diethylcarbamoyl, butyloxypropylcarbamoyl and dodecyloxy-propylcarbamoyl.

Examples of the sulfamoyl groups are the unsubstituted alkylsulfamoyl groups, such as ethylsulfamoyl, diethylsulfamoyl and dodecylsulfamoyl, and the substituted alkylsulfamoyl groups, such as dodecyloxypropylsulfamoyl.

Examples of the arylcarbamoyl groups are the phenylcarbamoyl groups and the substituted phenylcarbamoyl groups, and examples of the arylsulfamoyl groups are phenylsulfamoyl and the various substituted phenylsulfamoyl groups.

Examples of the acyl groups are acetyl, benzoyl, butanesulfonyl and benzenesulfonyl; examples of the acyloxy groups are acetoxy, lauroyloxy and butanesulfonyloxy; and examples of the alkoxycarbonyl groups are ethoxycarbonyl, i-propyloxycarbonyl and 2-ethylhexyloxycarbonyl.

—NHCOR$_5$ represents an alkylamido group with 1 to 22 carbon atoms. Typical examples of an unsubstituted alkylamido group are groups of acetamido, butaneamido, laurylamido and stearylamido. The useful groups may also include alicyclic amides such as cyclohexanecarbonamido group, groups with a branched structure such as 2-ethylhexanamido, and those having an unsaturated linkage.

Examples of a substituted alkylamido group are halogen-substituted alkylamido groups, such as groups of monochloroacetamido, trichloroacetamido, and perfluorobutaneamido, and phenoxy-substituted alkylamidos, such as groups of m-pentadecylphenoxyacetamido, α-(2,4-di-t-amylphenoxy)pentanamido, α-(2,4-di-t-acylphenoxy)acetamido, and o-chlorophenoxymyristic acid amido.

—NHCOR$_5$ may also represent an arylamido group which include benzamido, naphthoamido an unsubstituted arylamido such as, and such substituted arylamidos, as p-t-butylbenzamido and p-methylbenzamido both as an alkyl-substituted benzamido; p-methoxybenzamido, and o-dodecyloxy-benzamido both as an alkoxy-substituted benzamido; p-acetamidobenzamido, m-lauroylamidobenzamido and m-(2,4-di-t-amylphenoxyacetamido)benzamido all as an amido-substituted benzamido; and o-hexadecanesulfonamidobenzamido and p-butane-sulfonamidobenzamido both as a sulfonamido-substituted benzamido.

—NHCOOR$_5$ represents an alkoxycarbonylamino group, either in the substituted state or unsubstituted, with 1 to 22 carbon atoms, typical examples being, for example, ethoxycarbonylamino, i-propoxycarbonylamino, octyloxycarbonylamino, decyloxycarbonyl, and methoxyethyoxycarbonylamino. —NHCOOR$_5$ may also represent an aryloxycarbonyl group typified by phenoxycarbonyl.

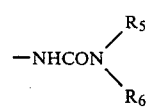

represents a dialkylcarbamoylamino group, typical examples being a dimethylcarbamoylamino group and a diethylcarboamoylamino group.

—NHSO$_2$R$_5$ represents an alkylsulfonamido group or an arylsulfonamido group.

Examples of the alkylsulfonamido group are methanesulfonamido, butanesulfonamido, and dodecanesulfonamido, each being an unsubstituted alkylsulfonamido with 1 to 22 carbon atoms, and benzylsulfonamido as a substituted alkylsulfonamido.

Examples of the arylsulfonamido group are benzenesulfonamido and naphthalenesulfonamido both as an unsubstituted arylsulfonamido and such substituted arylsulfonamido as p-toluenesulfonamido, 2,4,6-trimethylbenzensulfonamido and p-dodecylbenzensulfonamido all as an alkyl-substituted benzensulfonamido and p-dodecyloxybenzenesulfonamido and butyloxybenzensulfonamido both as an alkoxy-substituted benzensulfonamido.

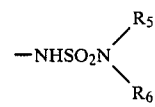

represents a sulfamoylamino group, preferable examples of which are dimethylsulfamoylamino and dibutylsulfamoylamino both as a dialkylsulfamoylamino.

Among the compounds represented by formula II, more suitable ones for the purpose can be expressed by the following formula.

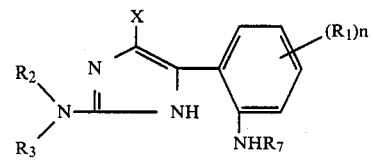

Formula IV

In formula IV, R$_1$, R$_2$, R$_3$, and X respectively have the same meaning as in formula II, wherein n denotes an integer from 0 to 4, while R$_7$ represents an alkyl group, an aryl group,

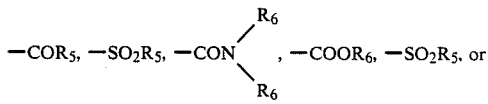

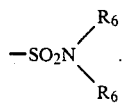

Examples of the alkyl and aryl groups respectively include the same alkyl or aryl groups as in formula II. In the case that —NHR$_7$ represents —NHCOR$_5$, —NHCOOR$_5$,

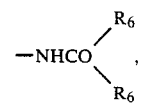

—NHSO$_2$R$_5$ or

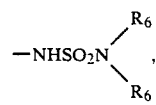

R$_5$ and R$_6$ respectively have the same meaning as in formula II.

The following discusses formula III in detail. In formula III, R$_4$, L, X and m respectively have the same meaninhave the same meaning as in formula I and R$_1$ represents the same as in formula II.

Among the compounds represented by formula III, more suitable ones for the purpose can be expressed by the following formula.

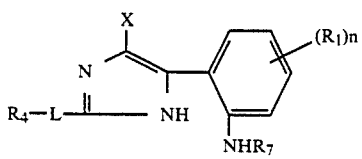

Formula V

In formula V, $R_1$, $R_4$, and X respectively have the same meanings as in formula III, wherein n denotes an integer from 0 to 4, while $R_7$ has the same meaning as in formula IV.

The following describes about formula VI. In formula VI, the group of

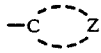

and X rerspectly have the same meaning as in formula I and $R_1$ is the same as in formula II.

Among the compounds represented by formula VI, more suitable ones for the purpose can be expressed by the following formula.

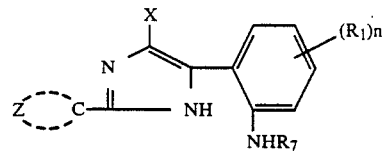

Formula VII

In formula VII, $R_1$ and the group of —C Z have the same meaning in formula VI, n is an integer of from 0 to 4, and $R_7$ has the same meaning in formula IV.

The following provides typical examples of the cyan coupler of the present invention. However, the scope of the present invention is not limited to the examples.

| Compound | X | A | B |
|---|---|---|---|
| 1 | —Cl | 2-(NHCOC$_{12}$H$_{25}$)phenyl | 3-pyridyl |
| 2 | —Cl | 2-[NHCOCH$_2$O-(2,4-di-C$_5$H$_{11}$(t)-phenyl)]phenyl | 3-pyridyl |
| 3 | —Cl | 2-[NHCOCH(C$_4$H$_9$)O-(2,4-di-C$_5$H$_{11}$(t)-phenyl)]phenyl | 4-pyridyl |
| 4 | —Cl | 2-[NHCOCH(C$_3$H$_7$(i))O-(2,4-di-C$_5$H$_{11}$(t)-phenyl)]phenyl | 2-pyridyl |
| 5 | —Cl | 2-[NHSO$_2$-(2-OC$_8$H$_{17}$-4-C$_8$H$_{17}$(t)-phenyl)]phenyl | 2-pyridyl |

-continued

| Compound | X | A | B |
|---|---|---|---|
| 6 | 4-butoxy-3-(alkylthio)phenyl with C8H17(t): —S—(2-OC4H9, 5-C8H17(t)-phenyl) | 2-OC4H9, 5-C8H17(t)-phenyl-SO2NH— (anilide) | 4-pyridyl |
| 7 | —Cl | 2-methyl-anilide of NHCOOCH2CH(C2H5)C4H9 | 4-pyridyl |
| 8 | —Cl | 2-methyl-phenyl-NHCONH-(3-NHCOCH3-phenyl) | 2-pyridyl |
| 9 | —Cl | 2-methyl-phenyl-NHCOCH(C2H5)O-(2-C5H11(t), 4-C5H11(t)-phenyl) | 2,6-dichloro-4-pyridyl |
| 10 | —Cl | 2-methyl-phenyl-NHCOCH(C3H7(i))O-(2-C5H11(t), 4-C5H11(t)-phenyl) | 2-(1H-benzimidazolyl) |
| 11 | —Cl | 2-methyl-phenyl-NHSO2-(4-OC12H25-phenyl) | 3,5-dimethylpyrazol-1-yl |
| 12 | —Cl | 2-methyl-phenyl-NHCOCH(C3H7(i))O-(2-C5H11(t), 4-C5H11(t)-phenyl) | 3,5-dimethylpyrazol-1-yl |
| 13 | —Cl | 2-methyl-phenyl-NHSO2-(2-OC4H9, 5-C8H17(t)-phenyl) | 2,6-dimethylmorpholin-4-yl |

-continued

| Compound | X | A | B |
|---|---|---|---|
| 14 | —Cl | 2-methylphenyl with NHCOC$_2$F$_5$ substituent | 2,6-dimethylpiperidin-1-yl (N-H) |
| 15 | —Cl | ethyl 3,5-dimethyl-1H-pyrrole-2-carboxylate | 2-methylphenyl-NHSO$_2$-(4-OC$_{12}$H$_{25}$-phenyl) |
| 16 | —Cl | 4,5-dimethyl-2-(NHCOCH$_3$)pyrimidine | 2-methylphenyl-NHSO$_2$-(2-OC$_4$H$_9$-5-C$_8$H$_{17}$(t)-phenyl) |
| 17 | —Cl | 2-methyl-3-(CH$_3$CONH)thiophene | 2-methylphenyl-NHSO$_2$N(C$_2$H$_5$)$_2$ |
| 18 | —Cl | 2-methyl-3-(5-chloro-2-methylphenyl)thiophene (with CH$_3$ substituents) | 2-methylphenyl-NHCOOCH$_2$CH(C$_2$H$_5$)C$_4$H$_9$ |
| 19 | —Cl | 2,5-dimethylfuran | 2-methylphenyl-NHCOCH$_2$O-(2,4-di-C$_5$H$_{11}$(t)-phenyl) |
| 20 | —Cl | 4-methyl-2-methylthiazole | 2-methylphenyl-NHCOCH(C$_3$H$_7$(i))O-(2,4-di-C$_5$H$_{11}$(t)-phenyl) |
| 21 | —Cl | 5-methyl-1-phenyl-1H-pyrazole | 2-methylphenyl-NHSO$_2$-(3,5-di-C$_5$H$_{11}$(t)-2-OC$_4$H$_9$-phenyl) |

-continued

| Compound | X | A | B |
|---|---|---|---|
| 22 | —Cl | 2-methylphenyl-NHCOCH(C₃H₇(i))O-[2,4-di-C₅H₁₁(t)-phenyl] | —NH-(2,4-dichlorophenyl) |
| 23 | —Cl | 2-methylphenyl-NHSO₂-[2-OC₄H₉-5-C₈H₁₇(t)-phenyl] | —NHCH₂CH(OC₂H₅)₂ |
| 24 | —Cl | 4-methylpyrimidin-2-yl-NHCOCH₂O-[2,4-di-C₅H₁₁(t)-phenyl] | —NH-(2-methyl-4-chlorophenyl) |
| 25 | —Cl | 2-methylphenyl-NHSO₂-[2-OC₄H₉-3,5-di-C₅H₁₁(t)-phenyl] | —NH-(4-OCH₃-phenyl) |
| 26 | —Cl | 2-methylphenyl-NHSO₂-[2-OC₈H₁₇-5-C₅H₁₁(t)-phenyl] | —NH-(2-CF₃-phenyl) |
| 27 | —S-[2-OC₄H₉-4-C₈H₁₇(t)-phenyl] | 2-methylphenyl-NHSO₂-[2-OC₈H₁₇-5-C₅H₁₁(t)-phenyl] | —NH-(2-OCH₃-5-CH-phenyl) |
| 28 | —Cl | 2-methylphenyl-NHCOOCH₂CH(C₂H₅)C₄H₉ | —NHCO-phenyl |
| 29 | —Cl | 2-methylphenyl-NHSO₂N(C₂H₅)₂ | —NHC₈H₁₇(t) |

-continued

| Compound | X | A | B |
|---|---|---|---|
| 30 | —Cl | 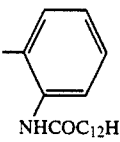 (2-methylphenyl with NHCOC₁₂H₂₅) | 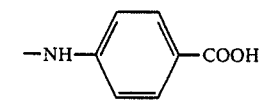 —NH—C₆H₄—COOH |
| 31 | —Cl | 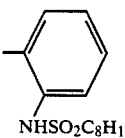 (2-methylphenyl with NHSO₂C₈H₁₇) | 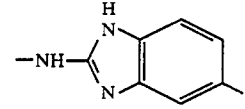 —NH-(5-chlorobenzimidazol-2-yl) |
| 32 | —Cl | 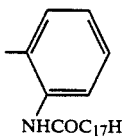 (2-methylphenyl with NHCOC₁₇H₃₅) | —SCH₃ |
| 33 | —Cl |  (2-methylphenyl-NHCO-phenyl-OC₁₄H₂₅) | 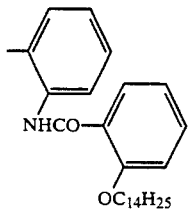 —SCH₂CH₂—N(morpholino) |
| 34 | —Cl | 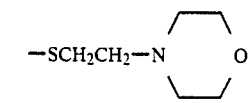 (2-methylphenyl-NHCOCH₂O-2,4-di-t-C₅H₁₁-phenyl) | —SCH₂CH₂COOH |
| 35 | —Cl | 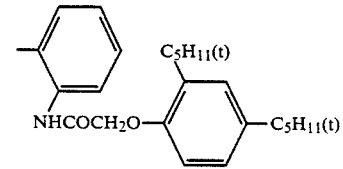 (2-methylphenyl with NHSO₂C₁₆H₃₃) | —SCH₂CO—C₆H₅ |
| 36 | —Cl | 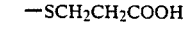 (2-methylphenyl-NHSO₂-phenyl-OC₁₂H₂₅) | 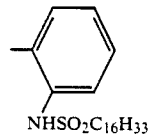 —SCH₂—(2-chlorophenyl) |
| 37 | H | 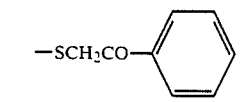 (2-methylphenyl-NHCOCH(C₃H₇(i))O-2,4-di-t-C₅H₁₁-phenyl) | —SC₁₆H₃₃ |
| 38 | —Cl | 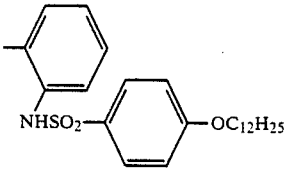 (2-methylphenyl with NHCON(C₂H₅)₂) | 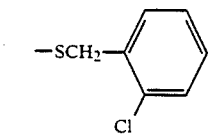 —S—(2-trifluoromethylphenyl) |

-continued
| Compound | X | A | B |
|---|---|---|---|
| 39 | —Cl | 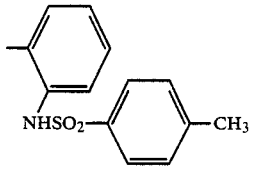 | 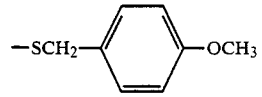 |
| 40 | —Cl | 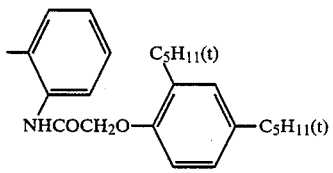 | 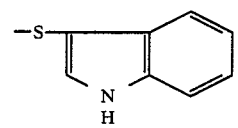 |
| 41 | —Cl | 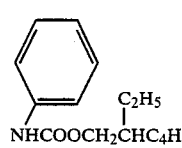 | 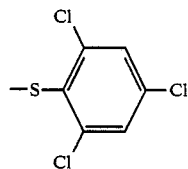 |
| 42 | —Cl | 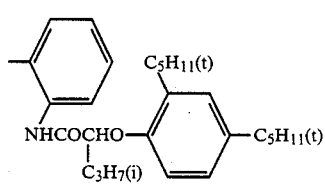 | 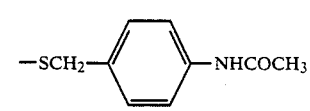 |
| 43 | —Cl | 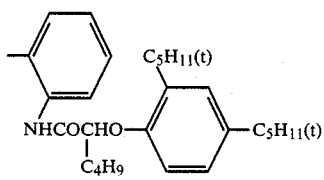 | —SCH$_2$CH$_2$NHSO$_2$CH$_3$ |
| 44 | —Cl | 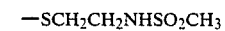 | 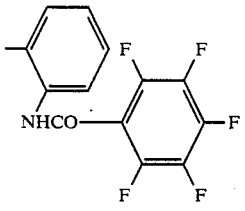 |
| 45 | —Cl | 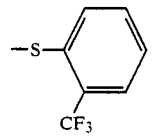 | 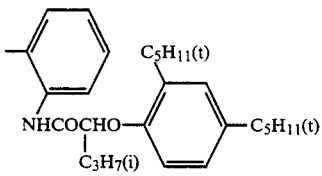 |
| 46 | —Cl | 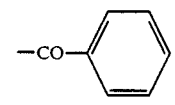 | 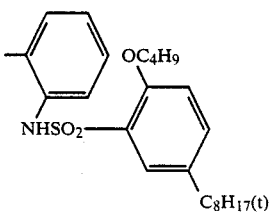 |

-continued
| Compound | X | A | B |
|---|---|---|---|
| 47 | —Cl | 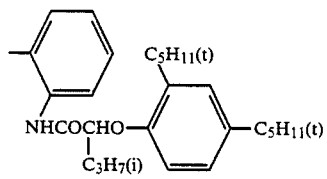 | —CN |
| 48 | —Cl | 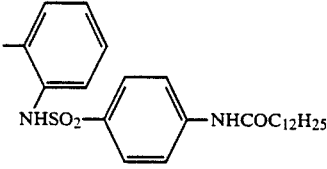 | 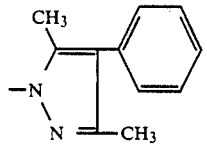 |
| 49 | —Cl | 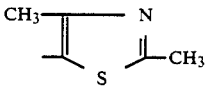 | —SC$_{16}$H$_{33}$ |
| 50 | —Cl | 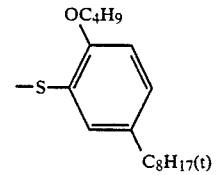 | 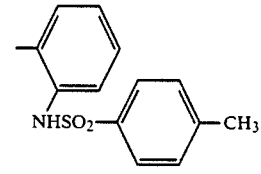 |
| 51 | —Cl | 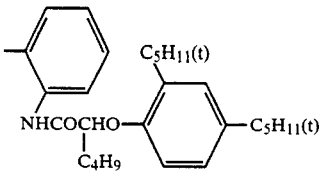 | —CH$_3$ |
| 52 | —Cl | 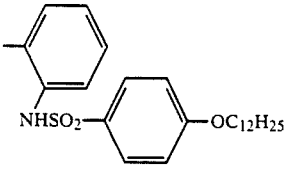 | —CH$_2$Cl |
| 53 | —Cl | 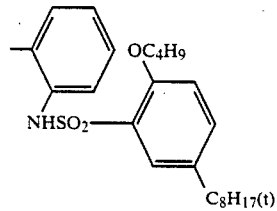 |  |
| 54 | —Cl | 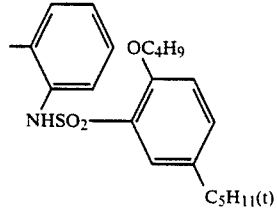 | 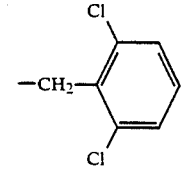 |

-continued
| Compound | X | A | B |
|---|---|---|---|
| 55 | —Cl | 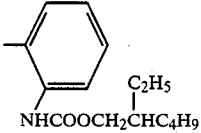 | —CHCH$_2$OCH$_3$<br>　\|<br>　Cl |
| 56 | —Cl | 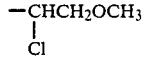 | 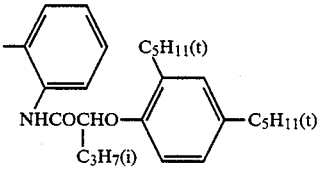 |
| 57 | —Cl | 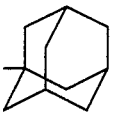 | —OC$_3$H$_7$(i) |
| 58 | —Cl | 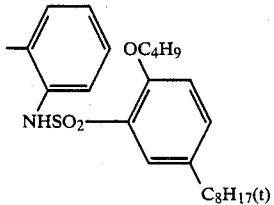 | —OCH$_3$ |
| 59 | —Cl |  | —SC$_{16}$H$_{33}$ |
| 60 | —Cl | 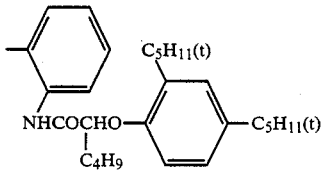 |  |
| 61 | —Cl | 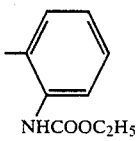 |  |
| 62 | —Cl | 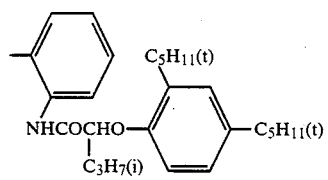 | 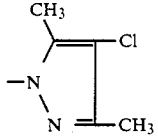 |

-continued
| Compound | X | A | B |
|---|---|---|---|
| 63 | —Cl | 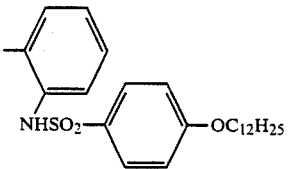 | 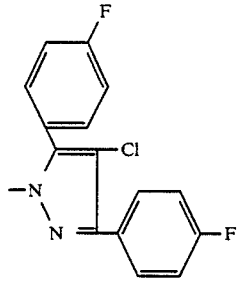 |
| 64 | —Cl | 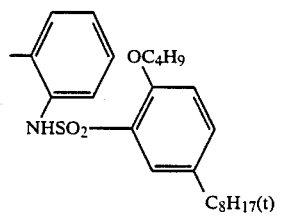 | 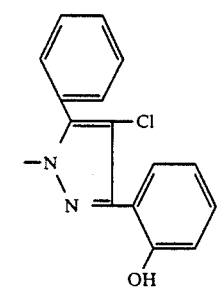 |
| 65 | —Cl | 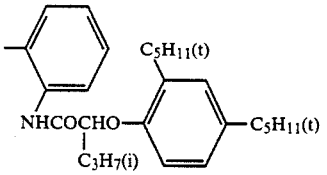 | 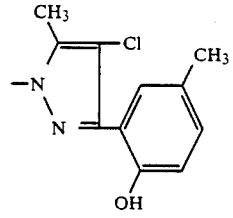 |
| 66 | —Cl | 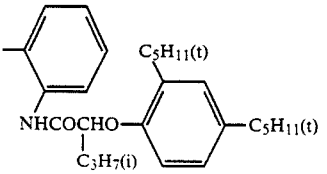 | 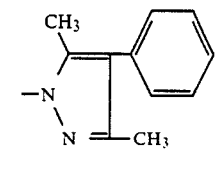 |
| 67 | —Cl | 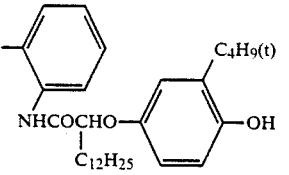 | 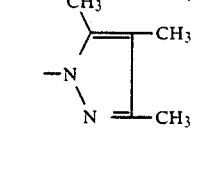 |
| 68 | —Cl | 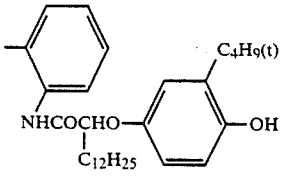 | 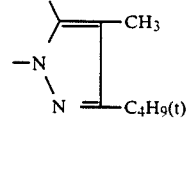 |
| 69 | —Cl | 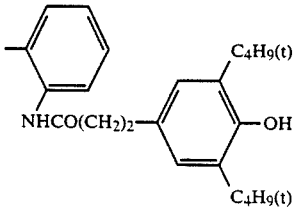 | 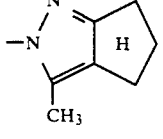 |

-continued

| Compound | X | A | B |
|---|---|---|---|
| 70 | —Cl | (o-tolyl)NHCOC(CH₃)₂CH₂SO₂—C₆H₄—NHCOCH₃ | 2-methyl-3-methyl-2,4,5,6-tetrahydrocyclopenta[c]pyrazole (H) |
| 71 | —Cl | (o-tolyl)NHCOOCH₂CH(C₂H₅)C₄H₉ | 2,3-dimethyl-indeno[1,2-c]pyrazol-4(2H)-one |
| 72 | —Cl | (o-tolyl)NHSO₂-[2-OC₈H₁₇-3,5-di-C₅H₁₁(t)-phenyl] | 2,3-dimethyl-4,5,6,7-tetrahydro-2H-indazole (H) |
| 73 | —Cl | (o-tolyl)NHCOCH(C₁₂H₂₅)O—(2-Cl-phenyl) | 2,3-dimethyl-4,5,6,7-tetrahydro-2H-indazole (H) |
| 74 | —Cl | (o-tolyl)NHCOCH(C₁₀H₂₁)O—C₆H₄—SO₂—C₆H₄—OH | 4-Cl-3,5-di(C₂H₅)-2-CH(C₂H₅)-pyrazole |
| 75 | —Cl | (o-tolyl)NHCOCH(CH₃)CH₂SO₂C₁₈H₃₇ | 4-Cl-3,5-di(C₂H₅)-2-CH(C₂H₅)-pyrazole |
| 76 | —Cl | (o-tolyl)NHCO(CH₂)₂SO₂CH₂CH(C₆H₁₃)C₈H₁₇ | 4-Cl-3,5-di(C₂H₅)-2-CH(C₂H₅)-pyrazole |

-continued

| Compound | X | A | B |
|---|---|---|---|
| 77 | —Cl | 2-methylphenyl-NHCOC(CH₃)₂CH₂SO₂C₁₈H₃₇ | 1-(N-N)-pyrazole with 3-C₂H₅, 4-Cl, 5-C₂H₅ |
| 78 | —Cl | 2-methylphenyl-NHCO(CH₂)₃SO₂-(2-OC₄H₉, 5-C₈H₁₇(t))phenyl | 1-(N-N)-pyrazole with 3-CF₃, 4-Cl, 5-(2-thienyl) |
| 79 | —Cl | 2-methylphenyl-NHCOOCH₂CH(CH₃)₂ | 1-(N-N)-pyrazole with 3-CF₃, 4-Cl, 5-(2-thienyl) |
| 80 | —Cl | 2-methylphenyl-NHCO-(2,3,5,6-tetrafluoro)phenyl | 1-(N-N)-pyrazole with 3-CH₃, 4-SO₂(4-Cl-C₆H₄), 5-CH₃ |
| 81 | —Cl | 2-methylphenyl-NHCOO-phenyl | 1-(N-N)-pyrazole with 3-CH₃, 4-SO₂(4-Cl-C₆H₄), 5-CH₃ |
| 82 | —Cl | 2-methylphenyl-NHCO(CH₂)₃O-(2,5-Cl₂, 4-OC₁₂H₂₅)phenyl | 1-(N-N)-pyrazole with 3-phenyl, 4-Cl, 5-(2-COOH-phenyl) |

-continued

| Compound | X | A | B |
|---|---|---|---|
| 83 | —Cl | 2-methylphenyl-NHCO-(2-OC₁₄H₂₉-phenyl) | —N(phenyl)—N=C(benzaldehyde-2-COOH)—C(Cl)=C(phenyl) group (hydrazone with Cl, phenyl, and 2-carboxyphenyl substituents) |
| 84 | —Cl | 2-methylphenyl-NHCOCH₂C₄H₉(t) | 3-methyl-4-[4-(t-C₄H₉)-(4-COOH-phenoxy)]-5-(2,4-dichlorophenyl) pyrazolinone-type group |
| 85 | —Cl | 2-methylphenyl-NHCONH-(4-CN-phenyl) | 3-methyl-4-[4-(t-C₄H₉)-(4-COOH-phenoxy)]-5-(2,4-dichlorophenyl) pyrazolinone-type group |
| 86 | —Cl | 2-methylphenyl-NHCOCH(C₁₂H₂₅)O-[3-(t-C₄H₉)-4-OH-phenyl] | 3-methyl-4,5,6,7-tetrahydro-2H-indazole (H at 3a) |
| 87 | —Cl | 2-methylphenyl-NHCOCH(C₁₀H₂₁)O-[4-(SO₂-4-OH-phenyl)-phenyl] | 3-methyl-4,5,6,7-tetrahydro-2H-indazole (H at 3a) |
| 88 | —Cl | 2-methylphenyl-NHCOC(CH₃)(CH₃)CH₂SO₂C₁₈H₃₇ | 3-methyl-4,5,6,7-tetrahydro-2H-indazole (H at 3a) |

-continued
| Compound | X | A | B |
|---|---|---|---|
| 89 | —Cl | 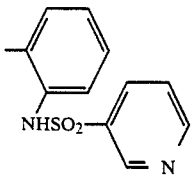 | 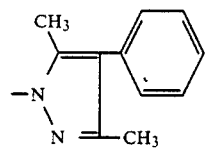 |
| 90 | —Cl | 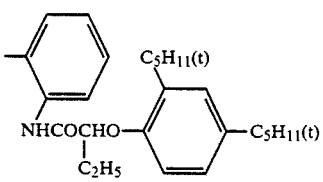 | 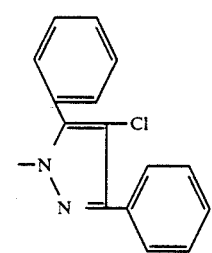 |
| 91 | —Cl | 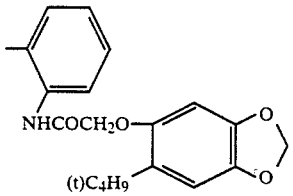 | 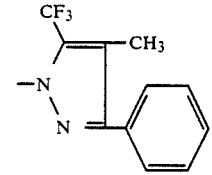 |
| 92 | —Cl | 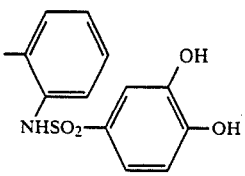 | 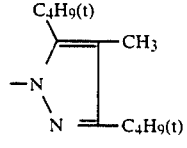 |
| 93 | —Cl | 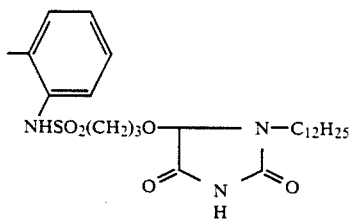 | 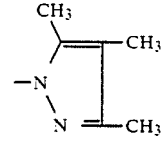 |
| 94 | —Cl | 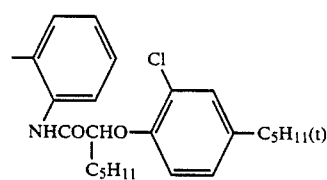 | 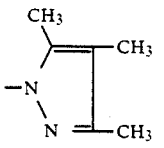 |
| 95 | —Cl | 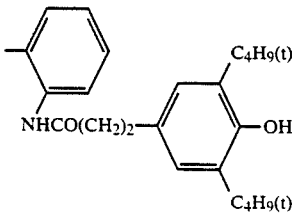 | 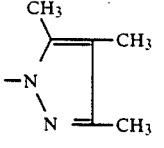 |

-continued

| Compound | X | A | B |
|---|---|---|---|
| 96 | —Cl | 2-methylphenyl-NHCO-(3,4,5-trihydroxyphenyl) | 1-methyl-3-t-C$_4$H$_9$-4-CH$_3$-5-t-C$_4$H$_9$-pyrazole |
| 97 | —Cl | 2-methylphenyl-NHCOCH(C$_{12}$H$_{25}$)O-(4-(N-sulfolanyl)phenyl) | 1-methyl-3-t-C$_4$H$_9$-4-CH$_3$-5-t-C$_4$H$_9$-pyrazole |
| 98 | —Cl | 2-methylphenyl-NHCO(CH$_2$)$_3$O-(2-N(C$_4$H$_9$)$_2$-4-t-C$_8$H$_{17}$-phenyl) | 1-methyl-3-CH$_3$-4-phenyl-5-CH$_3$-pyrazole |
| 99 | —Cl | 2-methylphenyl-NHSO$_2$-(2-C$_4$H$_9$O-3,5-di-t-C$_5$H$_{11}$-phenyl) | 1-methyl-3-phenyl-4-Cl-5-(6-methoxybenzofuran-5-yl)-pyrazole |
| 100 | —Cl | 2-methylphenyl-NHCOCH(CH$_3$)CH(CH$_3$)SO$_2$-(4-NHCOC$_2$F$_5$-phenyl) | 1-methyl-3-phenyl-4-CH$_3$-5-CF$_3$-pyrazole |
| 101 | —Cl | 2-methylphenyl-NHCOCH(C$_{12}$H$_{25}$)O-(4-(thiomorpholine-1,1-dioxide)phenyl) | 4,5,6,7-tetrahydro-2H-indazole (cyclopentane-fused) |
| 102 | —Cl | 2-methylphenyl-NHCOCH(CH$_3$)NHCO$_2$N(C$_2$H$_5$)$_2$ | 4,5,6,7-tetrahydro-2H-indazole (cyclohexane-fused)-3-CH$_3$ |

-continued
| Compound | X | A | B |
|---|---|---|---|
| 103 | —Cl | 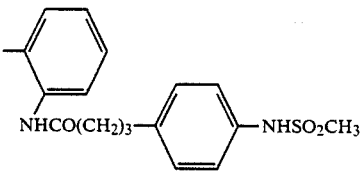 | 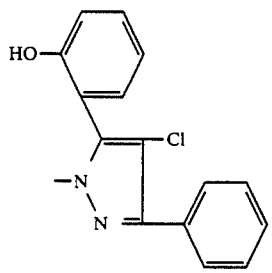 |
| 104 | —Cl | 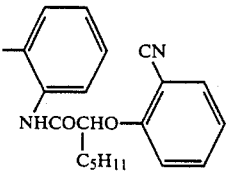 | 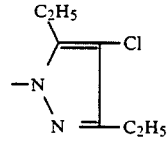 |
| 105 | —Cl | 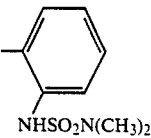 | 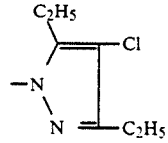 |
| 106 | —Cl | 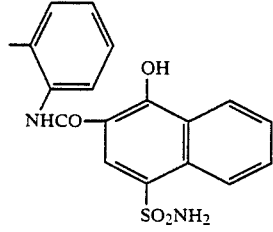 | 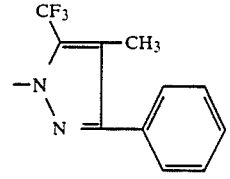 |
| 107 | —Cl | 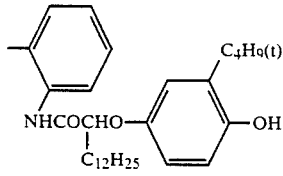 | 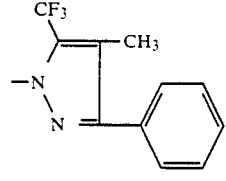 |
| 108 | —Cl | 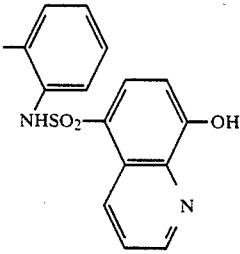 | 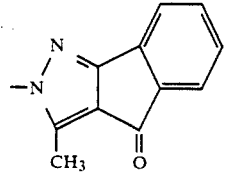 |
| 109 | —Cl | 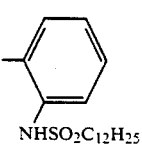 | 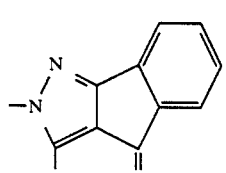 |

-continued
| Compound | X | A | B |
|---|---|---|---|
| 110 | —Cl | 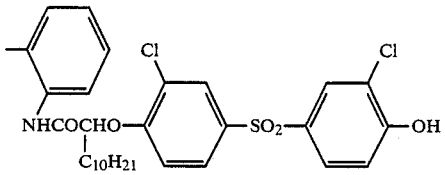 | 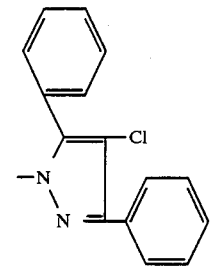 |
| 111 | —Cl | 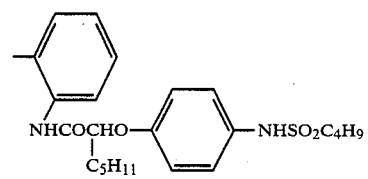 | 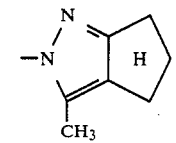 |
| 112 | —Cl | 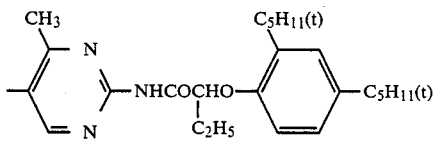 | —NHCOCH$_3$ |
| 113 | —Cl | 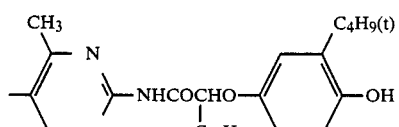 | —OC$_3$H$_7$ |
| 114 | —Cl | 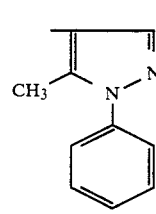 | —SC$_{16}$H$_{33}$ |
| 115 | —Cl | 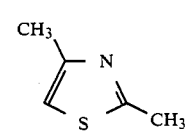 | —OC$_6$H$_{13}$ |
| 116 | —Cl | 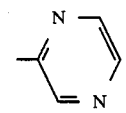 | 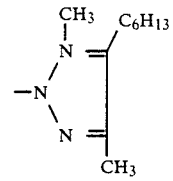 |
| 117 | —Cl | 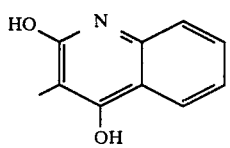 | —SCH$_2$—⟨C$_6$H$_4$⟩—OCH$_3$ |

-continued

| Compound | X | A | B |
|---|---|---|---|
| 118 | —Cl | [structure: N-chloro dihydroquinoline with CH₃, 4-chlorophenyl, and chlorophenyl substituents] | [structure: pyridine with NHCOC₁₅H₃₁] |
| 119 | —Cl | [structure: pteridine with CH₃ groups, NHCOCH₃ substituents] | [structure: pyridine with NHCOC₈H₁₇] |
| 120 | —Cl | [structure: 3-methylquinoline] | —OC₈H₁₇ |
| 121 | —Cl | [structure: pyridine with C₄H₉(t)NH, NHC₄H₉(t), CH₃] | [structure: pyrazole with CH₃, C₆H₁₃, CH₃] |
| 122 | —Cl | [structure: tolyl-NHCOCH(C₃H₇(i))O-phenyl with C₅H₁₁(t), C₅H₁₁(t)] | [structure: furan] |
| 123 | —Cl | [structure: phenol with CH₃, NHSO₂-phenyl-OC₁₂H₂₅] | [structure: thiophene] |
| 124 | —Cl | [structure: phenol with CH₃, NHCOCH₂O-phenyl with C₄H₉(t), C₄H₉(t)] | [structure: isothiazole] |
| 125 | —Cl | [structure: phenol with CH₃, NHCOCH₃] | [structure: isoxazole with CH₃, NHCOCH₂O-phenyl, C₅H₁₁(t), C₅H₁₁(t)] |

Cyan couplers of the present invention can be synthesized in accordance with the method disclosed in a report of Chemische Berichte (Pages 639 through 642 of the 34th volume, 1901) by Frang Kunkell. Typical synthesizing procedures of the method are as follows.

SYNTHESIS 1

Synthesis of:
2-hexadecylthio-4-[o-{α-(2,4-di-t-acylphenoxy)-β-methylbutaneamido}phenyl]imidazole (Synthesis of Compound 37)

10.6 g of o-{α-(2,4-di-t-amylphenoxy)-β-methylbutaneamido}-α-bromoacetophenone was suspended in 100 ml of acetonitryl, and 12.9 g of S-hexadecylisothiolea was added. Then 30 ml of dimethylformamido was added, and the mixture was subjected to heat at 60° C. for 5 minutes. The mixture was placed in 500 ml of water and extracted with 200 ml of ethyl acetate, dried with magnesium sulfate, and the solvent was then removed by reducing the environmental pressure. The residue was purified with silica gel column (developing solvent: ethyl acetate and hexane at the ratio of 1:6) to obtain 3.0 g of 2-hexadecylthio-4-[o-{α-(2,4-di-t-acylphenoxy)-β-methylbutane amido}phenyl]imidazole in the form of a paste.

SYNTHESIS 2

Synthesis of intermediate product of Compound 12

13.3 g of o-{α-(2,4-di-t-amylphenoxy)-β-methylbutaneamido}-α-bromoacetophenone was suspended in 100 ml of acetonitryl, and 6.9 g of 3,5-dimethylpyrazole-1-carboxyamidine was added. The mixture was stirred for 1 hour at room temperature. After the solvent was removed, the residue was extracted with ethyl acetate, and processed with silica gel column to obtain 3.3 g of the intermediate product of Compound 12 in the form of amolphous.

SYNTHESIS 3

Synthesis of Compound 12

3 g of the compound synthesized in the synthesis 1 was dissolved in 100 ml of chloroform, and 1 g of chlorosuccinimido (NCS) was added. The mixture was stirred for 15 hours at room temperature. After the solvent was removed, ethyl acetate and water were added to wash the residue, and the remaining organic layer was then dried with magnesium sulfate. After the solvent was removed, hexane was added to the residue to solidify the residue. The solidified residue was then purified with silica gel column to obtain 2.2 g of Compound 12.

SYNTHESIS 4

Synthesis of Compound 51

9.5 g of o-{α-(2,4di-t-amylphenoxy)hexanemamide}-α-bromoacetophenone was dissolved in 50 ml of chloroform, and 6 g of acetoamidine was added. The mixture was subjected to heat at 45° C. for 3 hours. After the solvent was removed, the residue was dissolved in 20 ml of acetonitryl. Then 1 ml of concentrated hydrochloric acid was dropped into the mixture to precipitate 1.4 g of solidified Compound 51.

SYNTHESIS 5

Synthesis of: 2-(4-chloro-3,5-dimethyl pyrazolyl)-4-[o-{α-(2,4-di-t-amylphenoxy)-β-methylbutaneamido}phenyl]-5-chloroimidazole (Synthesis of Compound 60)

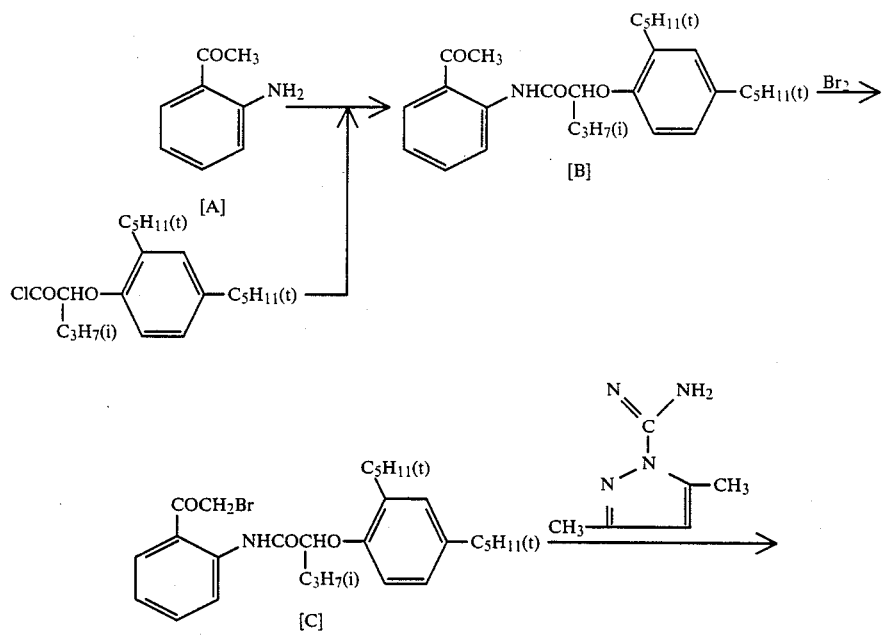

Procedure of synthesis

-continued
Procedure of synthesis

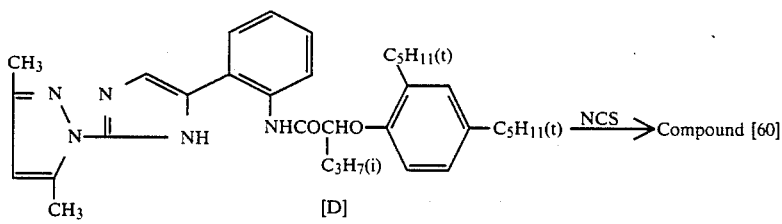

Synthesis of intermediate product B 25 g of o-aminoacetophenone was dissolved in 200 ml of ethyl acetate, and 15.36 g of pyridine was added. The mixture was stirred at room temperature. A solution was formed by dissolving 66.6 g of 2,4-di-t-amyl-phenoxy-~-chloride methylbutanate in 120 ml of ethyl acetate, and added to the mixture in drops over a period of 15 minutes. Then the solution with the mixture was stirred for 1 hour to create a reaction, and then washed with water to a degree where the pH value of the solution in reaction was between 6 to 7. After the solvent was removed under reduced environmental pressure to obtain an oily residue, and 350 ml of methanol was added to crystallize 54.2 g of the intermediate product B.

Synthesis of intermediate product C 47.1 g of the intermediate product B was dissolved in 240 ml of chloroform, and heated at 60° C. After that, 16.8 g of bromine was added in drops to the mixture over a time of 1 hour. After it was left standing for 3 hours, the solvent was removed under reduced environmental pressure to recrystallize and separate 37.2 g of the intermediate product C from the methanol.

Synthesis of intermediate product D 30.4 g of the intermediate product C was dissolved in 140 ml of chloroform, and 19.8 g of 3,5-dimethyl-pyrazole-1-carboxyamidine was added. The mixture was refluxed for 10 hours at a high temperature. After the formed solid object was filtered, the solvent was removed under reduced environmental pressure. 100 ml of acetonitryl was added to the residue to precipitate 13.8 g of the intermediate product D in the form of crystals.

Synthesis of example compound 60

13.8 g of the intermediate product D was dissolved in 80 ml of ethyl acetate, and 7.4 g of N-chlorosccinimide was added. The mixture was stirred for 24 hours at room temperature to create a reaction, and then washed with water and dehydrated with magnesium sulfate. After the dehydration, the solvent was removed by distillation, the residue was dried with magnesium sulfate. 60 ml of acetonitryl was then added to the residue to precipitate 10.4 g of the example compound 60 in the form of crystals.

In the above syntheses, the structure of each product was observed with NMR and MASS spectrums.

A coupler of the present invention may be used generally in the amount of $2 \times 10^{-3}$ to $8 \times 10^{-1}$ mol per mol silver halide, preferably in the amount of $1 \times 10^{-2}$ to $5 \times 10^{-1}$ mol per mol silver halide.

A coupler of the present invention can be used in combination, or together with another type of cyan coupler.

A coupler of the present invention can be incorporated into a silver halide photographic light-sensitive material by means of any of the methods of solid body dispersion, latex dispersion, o/w emulsion dispersion, etc. For example, the o/w emulsion dispersion method can be performed according to the following procedures. Generally, a hydrophobic additive such as a coupler is dissolved in a high boiling organic solvent with a boiling point of over 150° C. such as trichlesyl-phosphate, dibutylphtalete and, if necessary, together with an organic solvent having a low boiling point and/or water solubility such as ethyl acetate and butyl propionate. Then, the above mixture is emulsified by means of a surface active agent and dispersed in a water soluble binder such as gelatin water solution to be incorporated to the target hydrophilic colloid layer.

A silver halide photographic light-sensitive material of the present invention can be used as a color negative film, a color positive film, a color reversal film, a color print paper, etc., and is quite effective particularly when adopted for color print paper that is subjected directly to visual appreciation.

A silver halide photographic light-sensitive material of the invention, typified by a color print paper, has a multi-layer construction as follows in order to enable the subtractive color reproducing process. The multi-layer construction comprises a support; and an arbitrary number and in order of green-sensitive, red-sensitive, and blue-sensitive emulsion layers, which are provided on the support and respectively contain photographic couplers, i.e. a magenta coupler, a cyan coupler, and a yellow coupler of the present invention; and non-light-sensitive layers provided on the support. The number and order of the layers are arbitrarily changed based on important performance criteria and the requirement of usage of the light-sensitive material.

Preferable as a silver halide to be employed in a silver halide emulsion of the silver halide photographic light-sensitive material of the present invention is an arbitrary one of those generally used in a silver halide emulsion such as silver bromide, silver iodo-bromide, silver iodo-chloride, silver chloro-bromide, silver chloride, etc.

The silver halide emulsion is chemically sensitized with sulfur sensitizer, selenium sensitizer, reducing sensitizer, noble metal sensitizer, or the like. The emulsion can also be spectrally sensitized to an intended spectral region with a relevant sensitization dye that is known in the photographic industry.

The silver halide photographic light-sensitive material of this invention may arbitrarily contain an anti-color foggant, hardner, plasticizer, polymer latex, ultraviolet absorbent, formaline scavenger, mordant, development accelerator, development retardant, fluorescent whitening agent, matting agent, lubricant, anti-electrostatic agent, surface active agent, or the like.

The present invention may include any arbitrary processes such as color development, bleaching, fixing or bleach-fixing, stabilizing, washing, and stopping, which are popular in the photographic industry.

Since containing the novel cyan coupler, the silver halide photographic light-sensitive material of the invention exhibits excellent spectrum absorption characteristic of the cyan dye, i.e. sharp boundary on the shorter wavelength side. Therefore, a reduced amount of irregular absorption in the green and blue regions can be achieved, exhibiting excellent color reproducibility. Furthermore, since the optical density of the cyan dye is high, i.e. the cyan coupler of the invention has high color formablility, further improvement of sharpness is permitted by adopting thin layers, etc.

The cyan coupler of the invention is further advantageous in providing the dye to be developed with color fastness, and particularly excellent resistivity to heat and humidity, which enables provision of a photo-sensitive material exhibiting good storing stability.

EXAMPLES

The following discusses examples of the present invention, however, the scope of the invention is not limited to the examples.

EXAMPLE 1

(Preparation of silver halide emulsion)

Three sorts of silver halide emulsions, as shown in Table 1, were prepared in accordance with the methods of neutral and double jet mixing.

TABLE 1

| Emulsion No. | AgCl % | AgBr % | Average grain size μm | Chemical sensitizer | Spectral sensitizing dye |
|---|---|---|---|---|---|
| Em-1 | 99.5 | 0.5 | 0.67 | Sodium thiosulfate | SD-1*[3] |
| Em-2 | 99.5 | 0.5 | 0.46 | Chloroauric acid*[1] | SD-2*[4] |
| Em-3 | 99.5 | 0.5 | 0.43 | Sodium thiosulfate*[4] | SD-3*[5] |
| Em-4 | 10 | 90 | 0.67 | — | SD-1*[3] |
| Em-5 | 30 | 70 | 0.46 | Sodium thiosulfate | SD-2*[4] |
| Em-6 | 30 | 70 | 0.43 | Chloroauric acid*[1] | SD-3*[5] |

*[1] Incorporation amount was 2 mg per mol silver halide.
*[2] Incorporation amount was $5 \times 10^{-5}$ mol per mol silver halide.
*[3] Incorporation amount was 0.9 mmol per mol silver halide.
*[4] Incorporation amount was 0.7 mmol per mol silver halide.
*[5] Incorporation amount was 0.2 mmol per mol silver halide.

Each of the silver halide emulsions was chemically sensitized, and then $5 \times 10^{-3}$ mol of STB-1 per mol silver halide was added. The formula of STB-1, adopted as emulsion stabilizer, is shown hereinbelow.

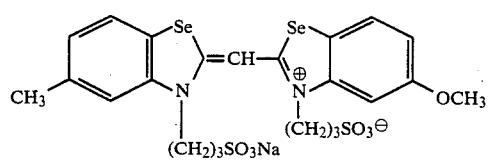

[SD-1]

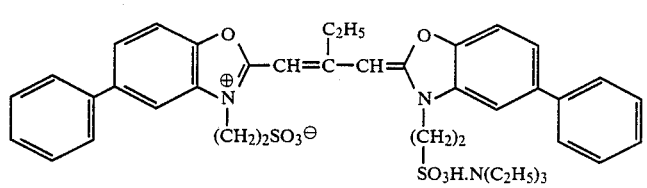

[SD-2]

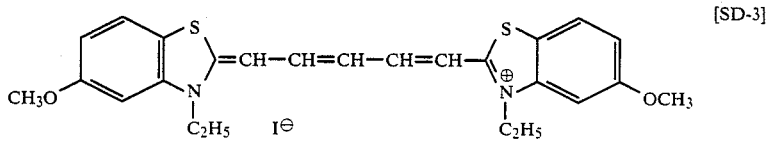

[SD-3]

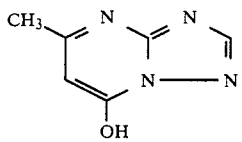

[STB-1]

(Preparation of a sample of a silver halide color photographic light-sensitive material)

The following layers 1 through 7 were then successively (simultaneously) layered on a paper support whose both surfaces were previously coated with polyethylene to thereby prepare silver halide color photographic light-sensitive materials 1 through 12. In the following examples, the listed amount of each added substance is the corresponding amount per 1 m² on a photosensitive material.

Layer 1: A layer containing 1.2 g of gelatin, 0.29 g (reduced mass of silver, this arrangement is applicable hereinunder) of blue-sensitive silver halide emulsion (Em-1), and 0.3 g of dinonylphthalate (DNP) dissolving therein 0.75 g of yellow coupler (Y-1) mentioned hereinbelow, 0.3 g of image stabilizer ST-1, and 0.015 g of 2,5-dioctylhydroquinone (HQ-1).

Layer 2: A layer containing 0.9 g of gelatin and 0.2 g of dioctylphthalate (DOP) dissolving therein 0.04 g of HQ-1.

Layer 3: A layer containing 1.4 g of gelatin, 0.2 g of green-sensitive silver halide emulsion (Em-2), 0.3 g of DOP dissolving therein 0.5 g of magenta coupler (M-1), 0.25 g of image stabilizer (ST-2), and 0.01 g of HQ-1; and filtering dye (AI-1) mentioned hereinbelow.

Layer 4: A layer containing 1.2 g of gelatin, and 0.3 g of DNP dissolving therein 0.6 g of ultraviolet absorbent (UV-1) mentioned hereinbelow, and 0.05 g of HQ-1.

Layer 5: A layer containing 1.4 g of gelatin, 0.20 g of red-sensitive silver halide emulsion (Em-3), and 0.3 g of DOP dissolving therein 0.7 mmol of cyan coupler listed in Table 2, and 0.01 g of HQ-1. It is noted that the amount of Comparative coupler CC-1 is 0.9 mmol.

Layer 6: A layer containing 1.1 g of gelatin and 5 mg of filtering dye (AI-2) mentioned hereinbelow, and 0.2 g of DOP dissolving therein 0.2 g of UV-1.

Layer 7: A layer containing 1.0 g of gelatin and 0.05 g of sodium, 2,4-dichloro-6-hydroxytriazine.

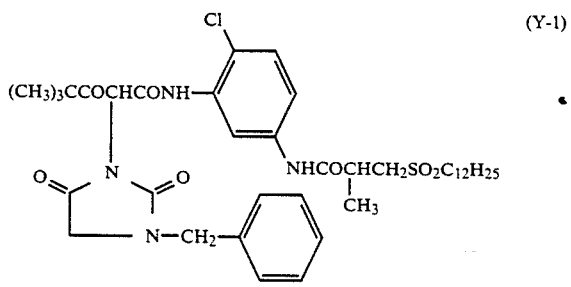

(Y-1)

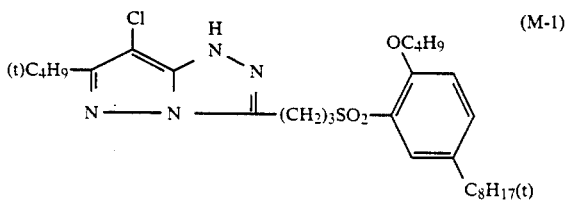

(M-1)

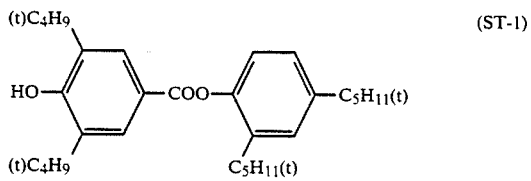

(ST-1)

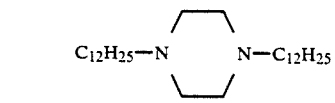

(ST-2)

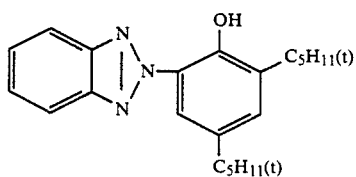

(UV-1)

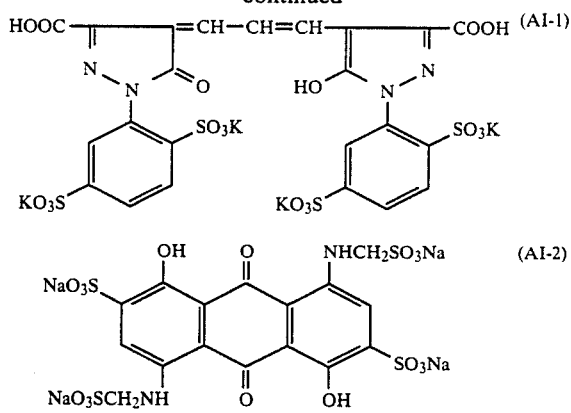

(AI-1)

(AI-2)

The so-obtained samples were subjected to exposure to red light through an optical wedge using an sensitometer (KS-7 produced by Konica Corporation), and then subjected to color developing in accordance with the processes as described below. Subsequently, the maximum density (Dmax) of the red-sensitive emulsion layer of each of the samples was measured using an optical densitometer (PDA-65 produced by Konica Corporation).

On the other hand, a color checker (Macbeth) was photographed onto a Konica color GX100 (Konica Corporation), and the film was subjected to developing. Then, the negative image of the Macbeth color checker was printed onto each of Samples 1 through 12 and 37 through 41 mentioned above so as to adjust the tone of the gray areas, thereby hues on each print were evaluated of the color reproducibility. The evaluation results are shown in Table 2.

| [Treatment procedure] | Temperature | Time |
|---|---|---|
| developing | 34.7 ± 0.3° C. | 45 sec. |
| Bleach-fixing | 34.7 ± 0.5° C. | 45 sec. |
| Stabilizing | 30 to 34° C. | 90 sec. |
| Drying | 60 to 80° C. | 60 sec. |
| Color-developer | | |
| Water | | 800 ml |
| Triethanolamine | | 8 g |
| N, N-diethylhydroxylamine | | 5 g |
| Potassium chloride | | 2 g |
| N-ethyl-N-~-methanesulfonamidoethyl-3-methyl-4-aminoaniline sulfate | | 5 g |
| Sodium tetrapolyphosphate | | 2 g |
| Potassium carbonate | | 30 g |
| Potassium sulfite | | 0.2 g |
| Optical brightening agent (4,4'-diaminostylbenzisulfone derivative) | | 1 g |

Water was added to prepare a one liter solution, that was adjusted to pH=10.2.

| [Bleach-fixer] | |
|---|---|
| Ferric ammonium ethylenediaminetetraacetate dihydrate | 60 g |
| Ethylenediaminetetraacetate | 3 g |
| Ammonium thiosulfate (70% solution) | 100 ml |
| Ammonium sulfite (40% solution) | 27.5 ml |

Water was added to prepare a one liter solution, that was adjusted to pH=5.7 with potassium carbonate or glacial acetic acid.

| [Stabilizer] | |
|---|---|
| 5-chloro-2-methyl-4-isothiazoline-3-one | 1 g |
| 1-hydroxyethylenedene-1, 1-diphosphate | 2 g |

Water was added to prepare a one liter solution, that was adjusted to pH=7.0 with sulfuric acid or potassium hydroxide.

TABLE 2

| | | Maximum | Color reproducibility | | | |
|---|---|---|---|---|---|---|
| Sample No. | Coupler | density | Green | Red | Magenta | Cyan |
| 1 (Comparative) | CC-1 | 1.90 | N.G. | P | P | P |
| 2 (Invention) | Example 3 | 2.20 | G | G | G | G |
| 3 (Invention) | Example 12 | 2.15 | G | G | G | G |
| 4 (Invention) | Example 59 | 2.13 | G | G | G | G |
| 5 (Invention) | Example 60 | 2.32 | G | G | G | G |
| 6 (Invention) | Example 58 | 2.12 | G | G | G | G |
| 7 (Invention) | Example 51 | 2.10 | G | G | G | G |
| 8 (Invention) | Example 66 | 2.16 | G | G | G | G |
| 9 (Invention) | Example 68 | 2.13 | G | G | G | G |
| 10 (Invention) | Example 72 | 2.21 | G | G | G | G |
| 11 (Invention) | Example 74 | 2.23 | G | G | G | G |
| 12 (Invention) | Example 90 | 2.25 | G | G | G | G |
| 37 (Invention) | Example 112 | 2.01 | G | G | G | G |
| 38 (Invention) | Example 115 | 1.95 | G | G | G | G |
| 39 (Invention) | Example 117 | 1.92 | G | G | G | G |
| 40 (Invention) | Example 124 | 1.94 | G | G | G | G |
| 41 (Invention) | Example 125 | 1.92 | G | G | G | G |

The color reproducibility is evaluated in three grades.
G: Color reproducibility (hue, saturation) is good
P: Color reproducibility (hue, saturation) is poor
MG: Color reproducibility (hue, saturation) is not good

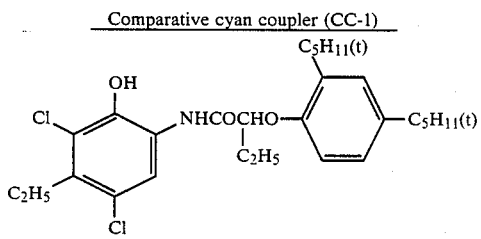

Comparative cyan coupler (CC-1)

As is obvious from the results shown in Table 2, each of Samples 2 through 12 of the present invention adopting cyan couplers containing imidazole exhibits improved color reproducibility in hues of green, red, magenta, and cyan in contrast to Comparative Example 1 employing a cyan coupler irrelative to the invention. Above all, the brightness of green is made higher so that it approaches that of the original color of green.

Furthermore, it is observed that each sample of the present invention exhibits high maximum density in the red-sensitive layer while proving excellent color formation efficiency.

Samples 1 through 12 were, after being subjected to exposure through an optical wedge and color developing, stored in a dark place at 77° C. or in a dark place at 60° C. and 80% RH (Relative Humidity) for 10 days to undergo a forced degradation test. After the test, the density of cyan dye located at a point of 1.0 in density (remaining rate of dye) was measured to evaluate the resistivity of each sample to heat and humidity. The results of the test are as shown in Table 3.

TABLE 3

| | | Remaining rate of dye (%) | |
|---|---|---|---|
| Sample No. | Coupler | 77° C. | 60° C., 80% RH |
| 1 (Comparative) | CC-1 | 90 | 95 |
| 2 (Invention) | Example 3 | 92 | 94 |
| 3 (Invention) | Example 12 | 93 | 95 |
| 4 (Invention) | Example 59 | 90 | 93 |
| 5 (Invention) | Example 60 | 93 | 96 |
| 6 (Invention) | Example 58 | 91 | 94 |
| 7 (Invention) | Example 51 | 90 | 93 |
| 8 (Invention) | Example 66 | 92 | 98 |
| 9 (Invention) | Example 68 | 95 | 98 |
| 10 (Invention) | Example 72 | 93 | 95 |
| 11 (Invention) | Example 74 | 94 | 96 |
| 12 (Invention) | Example 70 | 94 | 96 |
| 37 (Invention) | Example 112 | 90 | 93 |
| 38 (Invention) | Example 115 | 91 | 90 |
| 39 (Invention) | Example 117 | 93 | 96 |
| 40 (Invention) | Example 124 | 90 | 91 |
| 41 (Invention) | Example 125 | 90 | 90 |

As is obvious from the results shown in Table 3, each sample adopting a coupler of the present invention exhibits greater resistivity to heat and humidity in contrast to the comparative example.

EXAMPLE 2

Silver halide color photosensitive material samples 13 through 24 were prepared in the same manner as in Example 1 except that the blue-sensitive emulsion of 1st layer, the green-sensitive emulsion of the 3rd layer and the red-sensitive emulsion of the 5th layer were replaced by, Em-4, Em-5, Em-6 in Table 1.

The so-obtained samples were subjected to exposure through an optical wedge using an sensitometer (KS-7 produced by Konica Corporation), and then subjected to color developing in accordance with the processes as described below. Subsequently, the same measurements as in Example 1 were carried out.

The measurement results are shown in Table 4.

| Treatment procedure | | |
|---|---|---|
| Color developing | 3 min. and 30 sec. | Temp.: 33° C. |
| Bleach-fixing | 1 min. and 30 sec. | Temp.: 33° C. |
| Washing | 3 min. | Temp.: 33° C. |

| Prescription for color developing solution | |
|---|---|
| N-ethyl-N-β-methanesulfonamidoethyl-3-methyl-4- | 4.9 g |

| Prescription for color developing solution | |
|---|---|
| aminoaniline sulfate | |
| Hydroxyamine sulfate | 2.0 g |
| Potassium carbonate | 25.0 g |
| Potassium bromide | 0.6 g |
| Sodium sulfite anhydride | 2.0 g |
| Benzyl alcohol | 13 ml |
| Polyethylene glycol | 3.0 ml |
| (Average degree of polymerization: 400) | |

Water was added to prepare a one liter solution, that was adjusted to pH=10.0 with sodium hydroxide.

| Prescription for bleach-fixer | |
|---|---|
| Ferric sodium ethylenediaminetetraacetate | 6 g |
| Ammonium thiosulfate | 100 g |
| Sodium bisulfite | 10 g |
| Sodium metabisulfite | 3 g |

Water was added to prepare a one liter solution, that was adjusted to pH=7.0 with aqueous ammonia.

TABLE 4

| Sample No. | Coupler | Maximum density | Color reproducibility | | | |
|---|---|---|---|---|---|---|
| | | | Green | Red | Magenta | Cyan |
| 13 (Comparative) | CC-1 | 2.33 | N.G | P | P | P |
| 14 (Invention) | Example 3 | 2.51 | G | G | G | G |
| 15 (Invention) | Example 12 | 2.46 | G | G | G | G |
| 16 (Invention) | Example 59 | 2.43 | G | G | G | G |
| 17 (Invention) | Example 60 | 2.67 | G | G | G | G |
| 18 (Invention) | Example 58 | 2.41 | G | G | G | G |
| 19 (Invention) | Example 51 | 2.40 | G | G | G | G |
| 20 (Invention) | Example 66 | 2.49 | G | G | G | G |
| 21 (Invention) | Example 68 | 2.46 | G | G | G | G |
| 22 (Invention) | Example 72 | 2.57 | G | G | G | G |
| 23 (Invention) | Example 74 | 2.59 | G | G | G | G |
| 24 (Invention) | Example 90 | 2.61 | G | G | G | G |

Evaluation of the color reproducibility is expressed in the same way as in Table 2.

As is obvious from the results shown in Table 4, even when the state of emulsion and the treatment condition is changed, the samples of the invention exhibit high color densities in the red-sensitive layers, proving that they are excellent in color formation efficiency.

Furthermore, the samples also exhibit improved color reproducibility in hues of green, red, magenta, and cyan in the same way as Samples 2 through 12 in Example 1.

EXAMPLE 3

After undergoing back unit-static treatment, a triacetyl cellulose film support undercoated with maleic acid anhydride and vinyl acetate copolymer for subbing purpose was provided thereon with the layers of the following compositions in order to prepare Sample 25. The listed amount of each substance added is per mol silver halide unless otherwise specified.

| Unit-static treatment | |
|---|---|
| 1st backing layer: Stearic acid | 20 mg/m² |
| Diacetyl cellulose | 10 mg/m² |
| Almina sol | 1 g/m² |
| 2nd backing layer: Diacetyl cellulose | 50 mg/m² |
| Stearic acid | 10 mg/m² |
| Silica matting agent (average grain size: 3 μm) | 50 mg/m² |
| On the support | |
| 1st layer: anti-halation layer | |
| Ultraviolet absorbent-2 | 0.3 g/m² |
| Ultraviolet absorbent-3 | 0.4 g/m² |
| Black collodial silver | 0.24 g/m² |
| Gelatin | 2.7 g/m² |
| 2nd layer: intermediate layer | |
| 2,5-di-t-octylhydroquinone | 0.1 g/m² |
| Gelatin | 1.0 g/m² |
| 3rd layer: low speed red-sensitive silver halide emulsion layer | |
| Average grain size: 0.35 μm Monodispersed emulsion (Emulsion I) comprising AgBrI containing 2.5 mol % of AgI | (silver amount: 0.5 g/m²) |
| Sensitizing dye-4 | 7.6 × 10⁻⁴ mol |
| Coupler CC-2 | 0.1 mol |
| Gelatin | 0.9 g/m² |
| 4th layer: high speed red-sensitive silver halide emulsion layer | |
| Average grain size: .075 μm Monodispersed emulsion (Emulsion II) comprising AgBrI containing 2.5 mol % of AgI | (silver amount: 0.8 g/m²) |
| Sensitizing dye-4 | 3.2 × 10⁻⁴ mol |
| Coupler CC-2 | 0.2 mol |
| Gelatin | 1.75 g/m² |
| 5th layer: intermediate layer | |
| 2,5-di-t-octylhydroquinone | 1.1 g/m² |
| Gelatin | 0.9 g/m² |
| 6th layer: low speed green-sensitive silver halide emulsion layer | |
| Emulsion I | (silver amount: 1.0 g/m²) |
| Sensitizing dye-5 | 6.6 × 10⁻⁴ mol |
| Sensitizing dye-6 | 0.6 × 10⁻⁴ mol |
| Coupler M-2 | 0.05 mol |
| Gelatin | 0.8 g/m² |
| 7th layer: high speed green-sensitive silver halide emulsion layer | |
| Emulsion II | (silver amount: 1.0 g/m²) |
| Sensitizing dye-5 | 2.76 × 10⁻⁴ mol |
| Sensitizing dye-6 | 0.23 × 10⁻⁴ mol |
| Coupler M-2 | 0.15 mol |
| Gelatin | 1.5 g/m² |
| 8th layer: intermediate layer | |
| Same as 5th layer | |
| 9th layer: yellow filter layer | |
| Yellow colloidal silver | 0.1 g/m² |
| Gelatin | 0.9 g/m² |
| 2,5-di-t-octylhydroquinone | 0.1 g/m² |
| 10th layer: low speed blue-sensitive silver halide emulsion layer | |
| Average grain size: 0.6 μm Monodispersed emulsion (Emulsion II) comprising AgBrI containing 2.5 mol % of AgI | (silver amount: 0.4 g/m²) |
| Sensitizing dye-7 | 2.65 × 10⁻⁴ mol |
| Coupler Y-2 | 0.3 mol |

| | |
|---|---|
| Gelatin | 1.3 g/m² |
| 11th layer: high speed blue-sensitive silver halide emulsion layer | |
| Average grain size: 1.0 μm Monodispersed emulsion (Emulsion IV) comprising AgBrI containing 2.5 mol % of AgI | (silver amount: 0.8 g/m²) |
| Sensitizing dye-7 | 1.59 × 10⁻⁴ mol |
| Coupler Y-2 | 0.3 mol |
| Gelatin | 2.1 g/m² |
| 12th layer: 1st protective layer | |
| Ultraviolet absorbent-2, | 0.3 g/m² |
| Ultraviolet absorbent-3, | 0.4 g/m² |
| Gelatin | 1.2 g/m² |
| 2,5-di-t-octylhydroquinone | 0.1 g/m² |
| 13th layer: 2nd protective layer | |
| Substantially non-light-sensitive fine grain silver halide emulsion layer comprising AgBrI containing 1 mol % of AgI of average grain size of 0.06 μm | (silver amount: 0.3 g/m²) |
| Polyethyl methacrylate grains (size: 1.5 μm) | |

| | |
|---|---|
| Gelatin | 0.7 g/m² |
| Surface active agent-1 | |

Each of the above layers incorporated gelatin hardening agent-1 and surface active agent. Meanwhile, tricresylphosphate was used as solvent for the couplers.

Each of the emulsions is monodispersed emulsion having octahedral grains which were formed by dispersing seeds for emulsification (average content of silver iodide is 2 mol%) having the grain size of 0.095 μm or 0.25 μm at 45° C. in the presence of ammonium according to a double-jet method while controlling pAg and pH. The content of silver iodide in each core, intermediate layer and shell was controlled by changing the composition of the silver halide to be added.

Growth of the core/shell type silver halide emulsion was performed according to the methods disclosed in Japanese Patent O.P.I. Publication Nos. 59-52238, 60-138538, 58-49938, and 60-122935.

(Compounds used for preparing the samples)

Ultraviolet absorbent-2

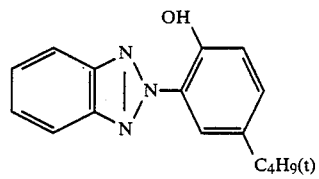

Ultraviolet absorbent-3

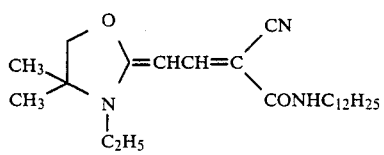

Sensitizing dye-4

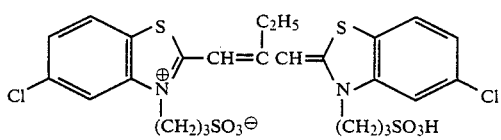

Sensitizing dye-5

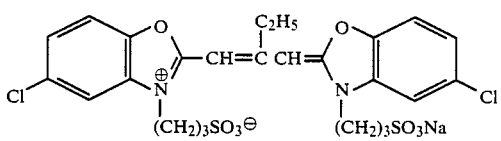

Sensitizing dye-6

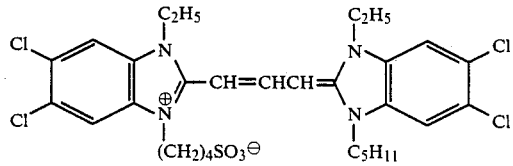

Sensitizing dye-7

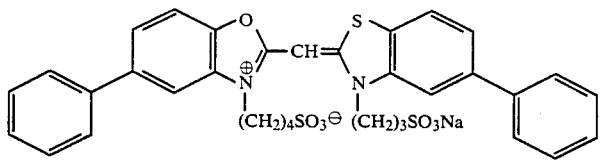

Coupler CC-2

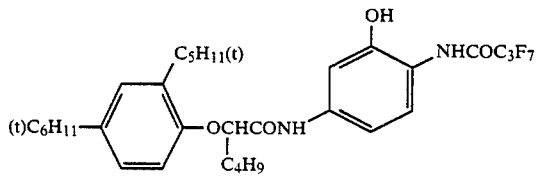

Coupler M-2

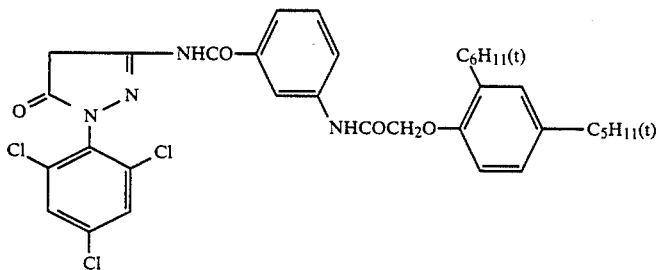

Coupler Y-2

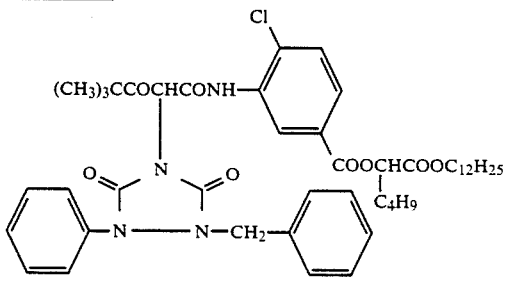

Gelatin hardening agent-1

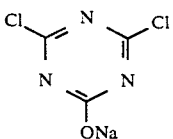

Surface active agent-1

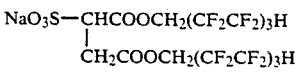

Then Samples 26 through 36 were prepared in the same manner as Sample 25 except that the coupler CC-2 in the third and fourth layers was replaced with a coupler of the present invention.

Color Checker (Macbeth) was photographed on Samples 25 through 36 and the samples were subjected to the color developing process as follows.

| Process | Time (minutes) | Temperature |
|---|---|---|
| First developing | 6 | 38° C. (±0.3) |
| Washing | 2 | 38° C. (±0.3) |
| Reversal | 2 | 38° C. (±0.3) |
| Color developing | 6 | 38° C. (±0.3) |
| Conditioning | 2 | 38° C. (±0.3) |

| -continued | | |
|---|---|---|
| Bleaching | 6 | 38° C. (±0.3) |
| Fixing | 4 | 38° C. (±0.3) |
| Washing | 4 | 38° C. (±0.3) |
| Stabilizing | 1 | room temp. |
| Drying | | |

| First developer | |
|---|---|
| Sodium tetrapolyphosphate | 2 g |
| Sodium sulfite | 20 g |
| Hydroquinone monosulfonic acid | 30 g |
| Sodium carbonate (monohydrate) | 30 g |
| 1-phenyl-4-methyl-4-hydroxymethyl-3-pyrazolidone | 2 g |
| Potassium bromide | 2.5 g |
| Potassium thiocyanate | 1.2 g |
| Potassium iodide (0.1% aqueous solution) | 2 m |

| | |
|---|---|
| -continued | |
| Water to make | 1000 ml |
| Reversal solution | |
| Hexasodium nitrilotrimethylenephosphate | 3 g |
| Stanous chloride (dihydrate) | 1 g |
| P-aminophenol | 0.1 g |
| Sodium hydroxide | 8 g |
| Glacial acetic acid | 15 ml |
| Water to make | 1000 ml |
| Color developer | |
| Sodium tetrapolyphosphate | 2 g |
| Sodium sulfite | 7 g |
| Sodium tertiary phosphate (dihydrate) | 36 g |
| Potassium bromide | 1 g |
| Potassium iodide (0.1% aqueous solution) 90 ml | 3 g |
| Sodium hydroxide | |
| Citrazinic acid | 1.5 g |
| N-methyl-N-(β-methanesulfonamidoethyl)-3-methyl-4-aminoaniline sulfate | 11 g |
| Ethylenediamine | 3 g |
| Water to make | 1000 ml |
| Conditioning solution | |
| Sodium sulfite | 12 g |
| Sodium ethylenediaminetetraacetate (dihydrate) | 8 g |
| Thioglycerol | 0.4 ml |
| Glacial acetic acid | 3 ml |
| Water to make | 1000 ml |
| Bleaching solution | |
| Sodium ethylenediaminetetraacetate (dihydrate) | 2.0 g |
| Ferric ammonium ethylenediaminetetraacetate (dihydrate) | 120.0 g |
| Potassium bromide | 100.0 g |
| Water to make | 1.0 l |
| Fixing solution | |
| Ammonium thiosulfate | 80.0 g |
| Sodium sulfite | 5.0 g |
| Sodium bisulfite | 5.0 g |
| Water to make | 1.0 l |
| Stabilizer | |
| Formaline (37 wt %) | 5.0 ml |
| Konidax (Konica Corporation) | 5.0 ml |
| Water to make | 1.0 l |

Evaluation results of the above samples with regard to color reproducibility in each hue are shown in Table 5.

TABLE 5

| | | Color reproducibility | | | |
|---|---|---|---|---|---|
| Sample No. | Coupler | Green | Red | Magenta | Cyan |
| 25 (Comparative) | CC-2 | N.G | P | P | P |
| 26 (Invention) | Example 3 | G | G | G | G |
| 27 (Invention) | Example 12 | G | G | G | G |
| 28 (Invention) | Example 59 | G | G | G | G |
| 29 (Invention) | Example 60 | G | G | G | G |
| 30 (Invention) | Example 58 | G | G | G | G |
| 31 (Invention) | Example 53 | G | G | G | G |
| 32 (Invention) | Example 66 | G | G | G | G |
| 33 (Invention) | Example 68 | G | G | G | G |
| 34 (Invention) | Example 72 | G | G | G | G |
| 35 (Invention) | Example 74 | G | G | G | G |
| 36 (Invention) | Example 90 | G | G | G | G |

Evaluation of color reproducibility were carried out as in Table 2.

In Table 5, each of Samples 26 through 36 adopting cyan couplers of the invention including imidazole couplers exhibits great improvement of color reproducibility in hues of green, red, magenta, and cyan in contrast to Comparative Example 25 employing a cyan coupler different from that of the invention. Above all, the brightness of green is made higher so that approaches that of the original color of green.

On the other hand, Sample 27 composed of a support provided thereon with solely the third layer of Sample 25, and Sample 38 of the same composition as Sample 37 (except that the coupler CC-2 is changed to the compound 60 of the invention) were prepared, then exposed through an optical wedge, and then treated in accordance with the aforesaid color developing process. The spectral transmittances of each of the samples were measured with an automatic recording color spectrum photometer type 320 (HITACHI). The measurement results are as shown in FIG. 1.

As obvious from FIG. 1, Sample 38 of the present invention exhibits a reduced amount of color absorption in the blue region at a wavelength of approx. 400 nm, and shows sharp boundary in the green region at a wavelength of approx. 500 to 600 nm. The reduction in the absorption amount of unnecessary light of blue and green is also apparent in the multi-layered Samples 26 through 36.

What is claimed is:

1. A silver halide photographic light-sensitive material comprising a support having thereon a silver halide emulsion layer, wherein said silver halide emulsion layer contains a cyan dye-forming coupler represented by the following Formula I:

Formula I wherein A is an organic group combined with the imidazole ring by a carbon atom, a nitrogen atom, an oxygen atom or a sulfur atom of said group; B is an

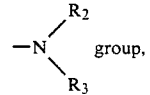

group, an —L—R$_4$ group or a

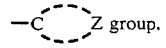

group, in which R$_2$ and R$_3$ are each a hydrogen or halogen atom, an alkyl group, or an aryl group, provided that said R$_2$ and R$_3$ are allowed to continue to complete a ring; L is an oxygen atom or a sulfur atom and R$_4$ is a hydrogen atom or a substituent; and Z is a group of non-metal atoms necessary to form a five- to seven-member heterocyclic ring together with the carbon atom bound to the imidazole ring, said heterocyclic ring contains an oxygen atom, a sulfur atom or a nitrogen atom,; X is a hydrogen atom or a group capable of being split off upon reaction with the oxidized product of a color developing agent.

2. The material of claim 1, wherein said B is an

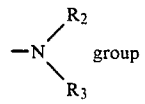

group in which R$_2$ and R$_3$ the same as denoted Formula I.

3. The material of claim 2, wherein said $R_2$ and $R_3$ are individually a halogen atom, an alkyl group or an aryl group.

4. The material of claim 2, wherein said A of Formula I is an alkyl group, an aryl group or a heterocyclic group.

5. The material of claim 4, wherein said coupler is represented by the following Formula II:

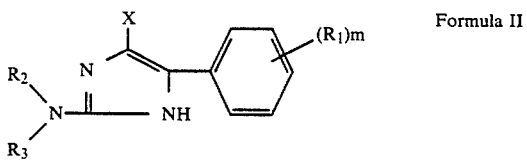

Formula II wherein $R_1$ is a substituent; $R_2$, $R_3$ and X are the same as denoted in Formula I; m is an integer of from 0 to 5.

6. The material of claim 4, wherein said $R_1$ is a halogen atom, a cyano group, a nitro group, a carboxyl group, an alkyl group, an alkoxyl group, a carbamoyl group, a sulfamoyl group, an acyl group, an acyloxy group, an alkoxycarbonyl group, an —NHCOR$_5$ group, an —NHSO$_2$R$_5$ group, an —NHCOOR$_5$ group, an

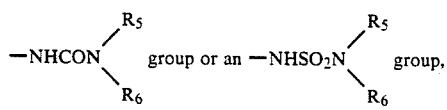

in which $R_5$ and $R_6$ are individually an alkyl group having 1 to 22 carbon atoms or an aryl group.

7. The material of claim 5, wherein $R_2$ and $R_3$ are individually a halogen atom, an alkyl group or an aryl group.

8. The material of claim 5, wherein said coupler is presented by the following Formula IV;

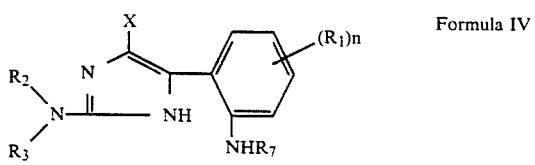

Formula IV wherein $R_1$, $R_2$, $R_3$, and X are the same as denoted in Formula II; n is an integer of from 0 to 4; and $R_7$ is an alkyl group, an aryl group, a —COR$_5$ group, an —SO$_2$R$_5$, a

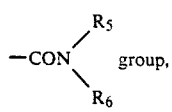

a —COOR$_5$ group, an —SO$_2$R$_5$ group or an

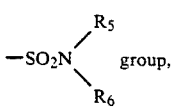

in which $R_5$ and $R_6$ are individually an alkyl group having 1 to 22 carbon atoms.

9. The material of claim 7, wherein $R_2$ and $R_3$ are individually a halogen atom, an alkyl group or an aryl group.

10. The material of claim 1, wherein said B is an —L—R$_4$ group, in which L and R$_4$ are the same as denoted in Formula I.

11. The material of claim 9, wherein said $R_4$ is a hydrogen atom, an alkyl group, an aryl group or a heterocyclic group.

12. The material of claim 9, wherein said A of Formula I is an alkyl group, an aryl group or a heterocyclic group.

13. The material of claim 8, wherein said coupler of Formula I is represented by the following Formula III;

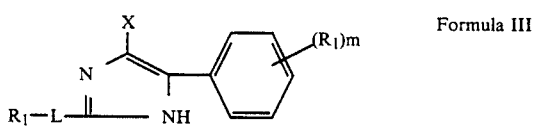

Formula III wherein $R_1$ is a substituent; L, $R_4$ and X are the same as denoted in Formula I; and m is an integer of from 0 to 5.

14. The material of claim 12, wherein said $R_1$ is a halogen atom, a cyano group, a nitro group, a carboxyl group, an alkyl group, an alkoxyl group, a carbamoyl group, a sulfamoyl group, an acyl group, an acyloxy group, an alkoxycarbonyl group, an —NHCOR$_5$ group, an —NHSO$_2$R$_5$ group, an —NHCOOR$_5$ group,

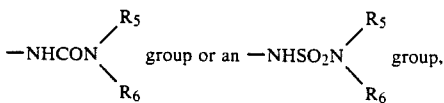

in which $R_5$ and $R_6$ are individually an alkyl group having 1 to 22 carbon atoms or an aryl group.

15. The material of claim 12, wherein said $R_4$ is a hydrogen atom, an alkyl group, an aryl group or a heterocyclic group.

16. The material of claim 14, wherein said heterocyclic group is a five- or six-member heterocyclic group.

17. The material of claim 12, wherein said coupler is represented by the following Formula V;

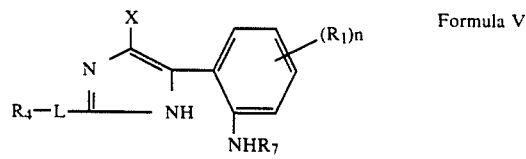

Formula V wherein $R_1$, $R_4$, L and X are the same as denoted in Formula III; and $R_7$ is an alkyl group, an aryl group, a —COR$_5$ group, an —SO$_2$R$_5$, a

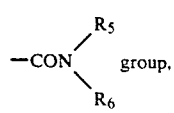

a —COOR$_5$ group, an —SO$_2$R$_5$ group or an

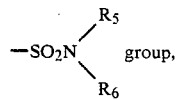

in which $R_5$ and $R_6$ are are individually an alkyl group having 1 to 22 carbon atoms or an aryl group.

18. The material of claim 14, wherein said $R_4$ is a hydrogen atom, an alkyl group, an aryl group or a heterocyclic group.

19. The material of claim 17, wherein said heterocyclic group is a five- or six member heterocyclic group.

20. The material of claim 1, wherein said B is a

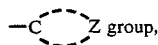

in which Z is the same as denoted in Formula I.

21. The material of claim 19, wherein said A of formula I is an alkyl group, an aryl group or a heterocyclic group.

22. The material of claim 20, wherein said coupler is represented by the following Formula VI:

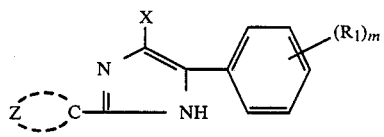

Formula VI wherein $R_1$ is a substituent; m is an integer of from 0 to 5; and X and Z are the same as denoted in Formula I.

23. The material of claim 21, wherein said $R_1$ is a halogen atom, a cyano group, a nitro group, a carboxyl group, an alkyl group, an alkoxyl group, a carbamoyl group, a sulfamoyl group, an acyl group, an acyloxy group, an alkoxycarbonyl group, an —NHCOR$_5$ group, an —NHSO$_2$R$_5$ group, an —NHCOOR$_5$ group, an

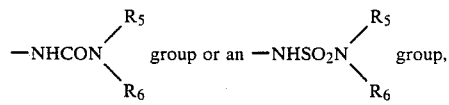

in which $R_5$ and $R_6$ are individually an alkyl group having 1 to 22 carbon atoms or an aryl group.

24. The material of claim 22, wherein said coupler is presented by the following Formula VII;

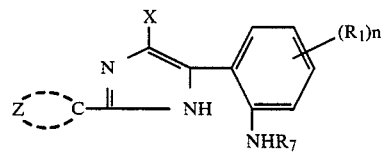

Formula VII wherein X, Z and $R_1$ are the same as denoted in Formula VI; n is an integer of from 0 to 4; and $R_7$ is an alkyl group, an aryl group, a —COR$_5$ group, an —SO$_2$R$_5$, a

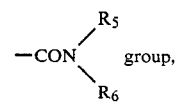

a —COOR$_5$ group, an —SO$_2$R$_5$ group or an

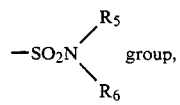

in which $R_5$ and $R_6$ are the sames as denoted in Formula VI.

* * * * *